US011957852B2

(12) United States Patent
Valls et al.

(10) Patent No.: US 11,957,852 B2
(45) Date of Patent: Apr. 16, 2024

(54) INTRAVASCULAR BALLOON WITH SLIDABLE CENTRAL IRRIGATION TUBE

(71) Applicant: Biosense Webster (Israel) Ltd., Yokneam (IL)

(72) Inventors: Jace P. Valls, San Jose, CA (US); Matthew W. Hitzeroth, Irwindale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 211 days.

(21) Appl. No.: 17/546,252

(22) Filed: Dec. 9, 2021

(65) Prior Publication Data

US 2022/0218959 A1 Jul. 14, 2022

Related U.S. Application Data

(60) Provisional application No. 63/137,270, filed on Jan. 14, 2021.

(51) Int. Cl.
*A61M 25/10* (2013.01)
*A61M 3/02* (2006.01)
(Continued)

(52) U.S. Cl.
CPC .......... *A61M 25/10* (2013.01); *A61M 3/0295* (2013.01); *A61B 5/367* (2021.01);
(Continued)

(58) Field of Classification Search
CPC ................ A61M 25/10; A61M 3/0295; A61M 2025/0018; A61M 2025/1068;
(Continued)

(56) References Cited

U.S. PATENT DOCUMENTS

D123,782 S 12/1940 Paul
3,316,896 A 5/1967 Louis
(Continued)

FOREIGN PATENT DOCUMENTS

CN 101422637 A 5/2009
CN 102271607 A 12/2011
(Continued)

OTHER PUBLICATIONS

Arena, C. B., "Theoretical Considerations of Tissue Electroporation With High-Frequency Bipolar Pulses" IEEE Transactions on Biomedical Engineering 58(5):1474-1482 (May 2011).
(Continued)

*Primary Examiner* — Nathan R Price
*Assistant Examiner* — Anh Bui
(74) *Attorney, Agent, or Firm* — Troutman Pepper Hamilton Sanders LLP

(57) ABSTRACT

A balloon catheter has a central tube that is configured to both structurally support and inflate a balloon membrane. The central tube has a lumen and sidewall inflation ports that provide a path for inflating the balloon. The lumen of the central tube is obstructed by a distal end piece, nose piece, or other structure to prevent fluid from exiting a distal end of the central tube. The central tube is configured such that, during inflation, inflation media is allowed to pass through an elongated shaft of the catheter, into a proximal open end of the central tube, and through the inflation ports into the balloon. The central tube can slide longitudinally in relation to the shaft to longitudinally elongate and/or truncate the balloon.

18 Claims, 9 Drawing Sheets

(51) Int. Cl.
    *A61B 5/367* (2021.01)
    *A61B 18/00* (2006.01)
    *A61B 18/14* (2006.01)
    *A61M 25/00* (2006.01)

(52) U.S. Cl.
    CPC .......... *A61B 2018/0022* (2013.01); *A61B 2018/00577* (2013.01); *A61B 18/1492* (2013.01); *A61B 2218/002* (2013.01); *A61M 2025/0018* (2013.01); *A61M 2025/1068* (2013.01); *A61M 2025/1086* (2013.01); *A61M 2025/1093* (2013.01); *A61M 2205/0216* (2013.01); *A61M 2205/0266* (2013.01); *A61M 2205/3317* (2013.01)

(58) Field of Classification Search
    CPC .. A61M 2025/1086; A61M 2025/1093; A61M 2205/0216; A61M 2205/0266; A61M 2205/3317; A61B 5/367; A61B 18/1492; A61B 2018/0022; A61B 2018/00577; A61B 2218/002; A61B 2018/00029
    See application file for complete search history.

(56) References Cited

U.S. PATENT DOCUMENTS

| | | | |
|---|---|---|---|
| 4,276,874 A | 7/1981 | Wolvek et al. |
| 4,299,227 A | 11/1981 | Lincoff |
| 4,587,975 A | 5/1986 | Salo et al. |
| 4,709,698 A | 12/1987 | Johnston et al. |
| 4,805,621 A | 2/1989 | Heinze et al. |
| 5,178,957 A | 1/1993 | Kolpe et al. |
| 5,429,617 A | 7/1995 | Hammersmark et al. |
| 5,582,609 A | 12/1996 | Swanson et al. |
| 5,584,830 A | 12/1996 | Ladd et al. |
| 5,702,386 A | 12/1997 | Stern et al. |
| 5,718,241 A | 2/1998 | Ben-Haim et al. |
| 5,797,903 A | 8/1998 | Swanson et al. |
| 5,860,974 A | 1/1999 | Abele |
| 5,971,983 A | 10/1999 | Lesh |
| 6,012,457 A | 1/2000 | Lesh |
| 6,024,740 A | 2/2000 | Lesh et al. |
| 6,042,580 A | 3/2000 | Simpson |
| 6,123,718 A | 9/2000 | Tu et al. |
| 6,164,283 A | 12/2000 | Lesh |
| 6,171,275 B1 | 1/2001 | Webster, Jr. |
| 6,176,832 B1 | 1/2001 | Habu et al. |
| 6,198,974 B1 | 3/2001 | Webster, Jr. |
| 6,226,542 B1 | 5/2001 | Reisfeld |
| 6,301,496 B1 | 10/2001 | Reisfeld |
| 6,322,558 B1 | 11/2001 | Taylor et al. |
| 6,380,957 B1 | 4/2002 | Banning |
| 6,402,740 B1 | 6/2002 | Ellis et al. |
| D462,389 S | 9/2002 | Provence et al. |
| 6,471,693 B1 | 10/2002 | Carroll et al. |
| 6,522,930 B1 | 2/2003 | Schaer et al. |
| 6,656,174 B1 | 12/2003 | Hegde et al. |
| 6,814,733 B2 | 11/2004 | Schwartz et al. |
| 6,892,091 B1 | 5/2005 | Ben-Haim et al. |
| 6,893,433 B2 | 5/2005 | Lentz |
| 6,986,744 B1 | 1/2006 | Krivitski |
| 6,987,995 B2 | 1/2006 | Drysen |
| 6,997,924 B2 | 2/2006 | Schwartz et al. |
| 7,142,903 B2 | 11/2006 | Rodriguez et al. |
| 7,156,816 B2 | 1/2007 | Schwartz et al. |
| 7,274,957 B2 | 9/2007 | Drysen |
| 7,410,486 B2 | 2/2008 | Fuimaono et al. |
| 7,340,307 B2 | 3/2008 | Maguire et al. |
| 7,377,906 B2 | 5/2008 | Selkee |
| 7,410,483 B2 | 8/2008 | Fuimaono et al. |
| 7,442,190 B2 | 10/2008 | Abboud et al. |
| 7,536,218 B2 | 5/2009 | Govari et al. |
| 7,591,799 B2 | 9/2009 | Selkee |
| 7,593,760 B2 | 9/2009 | Rodriguez et al. |
| 7,720,517 B2 | 5/2010 | Drysen |
| 7,756,576 B2 | 7/2010 | Levin |
| 7,842,031 B2 | 11/2010 | Abboud et al. |
| 7,853,302 B2 | 12/2010 | Rodriguez et al. |
| 8,000,765 B2 | 8/2011 | Rodriguez et al. |
| 8,021,327 B2 | 9/2011 | Selkee |
| 8,048,032 B2 | 11/2011 | Root et al. |
| 8,231,617 B2 | 7/2012 | Satake |
| 8,267,932 B2 | 9/2012 | Baxter et al. |
| 8,275,440 B2 | 9/2012 | Rodriguez et al. |
| 8,348,888 B2 | 1/2013 | Selkee |
| 8,357,152 B2 | 1/2013 | Govari et al. |
| D682,289 S | 5/2013 | DiJulio et al. |
| D682,291 S | 5/2013 | Baek et al. |
| D690,318 S | 9/2013 | Kluttz et al. |
| D694,652 S | 12/2013 | Tompkin |
| 8,641,709 B2 | 2/2014 | Sauvageau et al. |
| 8,721,590 B2 | 5/2014 | Seward et al. |
| 8,777,161 B2 | 7/2014 | Pollock et al. |
| D716,340 S | 10/2014 | Bresin et al. |
| 8,852,181 B2 | 10/2014 | Malecki et al. |
| D720,766 S | 1/2015 | Mandal et al. |
| D721,379 S | 1/2015 | Moon et al. |
| D724,618 S | 3/2015 | Shin |
| 8,998,893 B2 | 4/2015 | Avitall |
| D729,263 S | 5/2015 | Ahn et al. |
| 9,089,350 B2 | 7/2015 | Willard |
| D736,780 S | 8/2015 | Wang |
| 9,126,023 B1 | 9/2015 | Sahatjian et al. |
| D740,308 S | 10/2015 | Kim et al. |
| D743,424 S | 11/2015 | Danielyan et al. |
| D744,000 S | 11/2015 | Villamor et al. |
| 9,173,758 B2 | 11/2015 | Brister et al. |
| D747,742 S | 1/2016 | Fan et al. |
| D750,644 S | 3/2016 | Bhutani et al. |
| 9,283,034 B2 | 3/2016 | Katoh et al. |
| 9,289,141 B2 | 3/2016 | Lowery et al. |
| D753,690 S | 4/2016 | Vazquez et al. |
| 9,320,631 B2 | 4/2016 | Moore et al. |
| 9,345,540 B2 | 5/2016 | Mallin et al. |
| D759,673 S | 6/2016 | Looney et al. |
| D759,675 S | 6/2016 | Looney et al. |
| D764,500 S | 8/2016 | Wang |
| D765,709 S | 9/2016 | Gagnier |
| D767,616 S | 9/2016 | Jones et al. |
| D768,696 S | 10/2016 | Gagnier |
| D783,037 S | 4/2017 | Hariharan et al. |
| 9,655,677 B2 | 5/2017 | Salahieh et al. |
| D791,805 S | 7/2017 | Segars |
| 9,795,442 B2 | 10/2017 | Salahieh et al. |
| 9,907,610 B2 | 3/2018 | Beeckler et al. |
| 9,956,035 B2 | 5/2018 | Govari et al. |
| D861,717 S | 10/2019 | Brekke et al. |
| 10,688,278 B2 | 6/2020 | Beeckler et al. |
| 2001/0031961 A1 | 10/2001 | Hooven |
| 2002/0002369 A1 | 1/2002 | Hood |
| 2002/0065455 A1 | 5/2002 | Ben-Haim et al. |
| 2002/0068931 A1 | 6/2002 | Wong et al. |
| 2002/0077627 A1 | 6/2002 | Johnson et al. |
| 2002/0160134 A1 | 10/2002 | Ogushi et al. |
| 2003/0018327 A1 | 1/2003 | Truckai et al. |
| 2003/0028183 A1 | 2/2003 | Sanchez et al. |
| 2003/0050637 A1 | 3/2003 | Maguire et al. |
| 2003/0060820 A1 | 3/2003 | Maguire et al. |
| 2003/0144658 A1 | 7/2003 | Schwartz et al. |
| 2004/0122445 A1 | 6/2004 | Butler et al. |
| 2004/0147920 A1 | 7/2004 | Keidar |
| 2004/0225285 A1 | 11/2004 | Gibson |
| 2005/0070887 A1 | 3/2005 | Taimisto et al. |
| 2005/0119686 A1 | 6/2005 | Clubb |
| 2006/0013595 A1 | 1/2006 | Trezza et al. |
| 2006/0106375 A1 | 5/2006 | Werneth et al. |
| 2006/0135953 A1 | 6/2006 | Kania et al. |
| 2007/0071792 A1 | 3/2007 | Varner et al. |
| 2007/0080322 A1 | 4/2007 | Walba |
| 2007/0083194 A1 | 4/2007 | Kunis et al. |
| 2007/0287994 A1 | 12/2007 | Patel |
| 2008/0018891 A1 | 1/2008 | Hell et al. |
| 2008/0021313 A1 | 1/2008 | Eidenschink et al. |

(56) References Cited

U.S. PATENT DOCUMENTS

| | | |
|---|---|---|
| 2008/0051707 A1 | 2/2008 | Phan et al. |
| 2008/0140072 A1 | 6/2008 | Stangenes et al. |
| 2008/0183132 A1 | 7/2008 | Davies et al. |
| 2008/0188912 A1 | 8/2008 | Stone et al. |
| 2008/0202637 A1 | 8/2008 | Hector et al. |
| 2008/0208186 A1 | 8/2008 | Slater |
| 2008/0249463 A1 | 10/2008 | Pappone et al. |
| 2008/0262489 A1 | 10/2008 | Steinke |
| 2008/0281312 A1 | 11/2008 | Werneth et al. |
| 2009/0163890 A1 | 6/2009 | Clifford et al. |
| 2009/0182318 A1 | 7/2009 | Abboud et al. |
| 2009/0270850 A1 | 10/2009 | Zhou et al. |
| 2009/0299401 A1* | 12/2009 | Tilson .............. A61M 25/1029 606/192 |
| 2010/0069836 A1 | 3/2010 | Satake |
| 2010/0114269 A1 | 5/2010 | Wittenberger et al. |
| 2010/0204560 A1 | 8/2010 | Salahieh et al. |
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0130648 A1 | 6/2011 | Beeckler et al. |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0313286 A1 | 12/2011 | Whayne et al. |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1 | 4/2012 | Beetel et al. |
| 2012/0101538 A1 | 4/2012 | Ballakur et al. |
| 2012/0143177 A1 | 6/2012 | Avitall |
| 2012/0143293 A1 | 6/2012 | Mauch et al. |
| 2012/0165732 A1* | 6/2012 | Muller .............. A61B 17/8855 604/99.01 |
| 2012/0191079 A1 | 7/2012 | Moll et al. |
| 2012/0209260 A1 | 8/2012 | Lambert et al. |
| 2013/0085360 A1 | 4/2013 | Grunewald |
| 2013/0090649 A1 | 4/2013 | Smith et al. |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0318439 A1 | 11/2013 | Landis et al. |
| 2014/0012242 A1 | 1/2014 | Lee et al. |
| 2014/0018788 A1 | 1/2014 | Engelman et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0227437 A1 | 8/2014 | DeBoer et al. |
| 2014/0243821 A1 | 8/2014 | Salahieh et al. |
| 2014/0275993 A1 | 9/2014 | Ballakur |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0330266 A1 | 11/2014 | Thompson et al. |
| 2014/0357956 A1 | 12/2014 | Salahieh et al. |
| 2015/0005799 A1 | 1/2015 | Lindquist et al. |
| 2015/0025532 A1 | 1/2015 | Hanson et al. |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119875 A1 | 4/2015 | Fischell et al. |
| 2015/0141982 A1 | 5/2015 | Lee |
| 2015/0157382 A1 | 6/2015 | Avitall et al. |
| 2015/0216591 A1 | 8/2015 | Cao et al. |
| 2015/0216650 A1 | 8/2015 | Shaltis |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0327805 A1 | 11/2015 | Ben-Haim |
| 2015/0341752 A1 | 11/2015 | Flynn |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0166306 A1 | 6/2016 | Pageard |
| 2016/0175041 A1 | 6/2016 | Govari et al. |
| 2016/0196635 A1 | 7/2016 | Cho et al. |
| 2016/0250455 A1 | 9/2016 | Ahn |
| 2016/0256305 A1 | 9/2016 | Longo et al. |
| 2016/0374748 A9 | 12/2016 | Salahieh et al. |
| 2017/0042614 A1 | 2/2017 | Salahieh et al. |
| 2017/0042615 A1 | 2/2017 | Salahieh et al. |
| 2017/0080192 A1 | 3/2017 | Giasolli et al. |
| 2017/0143359 A1 | 5/2017 | Nguyen et al. |
| 2017/0164464 A1 | 6/2017 | Weinkam et al. |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2018/0074693 A1 | 3/2018 | Jones et al. |
| 2018/0110562 A1 | 4/2018 | Govari et al. |
| 2018/0125575 A1 | 5/2018 | Schwartz et al. |
| 2018/0140807 A1* | 5/2018 | Herrera .............. A61M 25/1011 |
| 2018/0161093 A1 | 6/2018 | Basu et al. |
| 2018/0256247 A1 | 9/2018 | Govari et al. |
| 2018/0280080 A1 | 10/2018 | Govari et al. |
| 2018/0333162 A1 | 11/2018 | Saab |
| 2018/0368927 A1 | 12/2018 | Lyons et al. |
| 2019/0059818 A1* | 2/2019 | Herrera .............. A61B 18/1492 |
| 2019/0060622 A1 | 2/2019 | Beeckler |
| 2019/0143079 A1 | 5/2019 | Beeckler et al. |
| 2019/0175262 A1 | 6/2019 | Govari et al. |
| 2019/0175263 A1 | 6/2019 | Altmann et al. |
| 2019/0183567 A1 | 6/2019 | Govari et al. |
| 2019/0201669 A1 | 7/2019 | Govari et al. |
| 2019/0217065 A1 | 7/2019 | Govari et al. |
| 2019/0297441 A1 | 9/2019 | Dehe et al. |
| 2019/0298441 A1 | 10/2019 | Clark et al. |
| 2019/0365451 A1 | 12/2019 | Jung, Jr. |
| 2020/0001054 A1 | 1/2020 | Jimenez et al. |
| 2020/0015693 A1 | 1/2020 | Beeckler et al. |
| 2020/0085497 A1 | 3/2020 | Zhang et al. |
| 2020/0147295 A1 | 5/2020 | Van Niekerk et al. |
| 2020/0155226 A1 | 5/2020 | Valls et al. |
| 2021/0077180 A1 | 3/2021 | Govari et al. |
| 2021/0169567 A1 | 6/2021 | Govari et al. |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |
| CN | 104546117 A | 4/2015 |
| CN | 105105844 A | 12/2015 |
| CN | 105473091 A | 4/2016 |
| CN | 105473093 A | 4/2016 |
| EP | 0779059 A1 | 6/1997 |
| EP | 1790304 A2 | 5/2007 |
| EP | 2749214 A1 | 7/2014 |
| EP | 2865350 A2 | 4/2015 |
| EP | 2875790 A2 | 5/2015 |
| EP | 3238646 A2 | 11/2017 |
| EP | 3238648 A1 | 11/2017 |
| EP | 3251622 A1 | 12/2017 |
| EP | 3300680 A1 | 4/2018 |
| EP | 3315087 A1 | 5/2018 |
| EP | 3332727 A2 | 6/2018 |
| EP | 3571983 A2 | 11/2019 |
| EP | 3586778 A1 | 1/2020 |

(56) References Cited

FOREIGN PATENT DOCUMENTS

| | | |
|---|---|---|
| EP | 3593853 A1 | 1/2020 |
| EP | 3653153 A1 | 5/2020 |
| JP | H06261951 A | 9/1994 |
| JP | H1176233 A | 3/1999 |
| JP | 2000504242 A | 4/2000 |
| JP | 2005052424 A | 3/2005 |
| JP | 2010507404 A | 3/2010 |
| JP | 2012024156 A | 2/2012 |
| JP | 2013013726 A | 1/2013 |
| JP | 2013078587 A | 5/2013 |
| JP | 2013529109 A | 7/2013 |
| JP | 2014529419 A | 11/2014 |
| JP | 2015503365 A | 2/2015 |
| JP | 2015100706 A | 6/2015 |
| JP | 2015112113 A | 6/2015 |
| JP | 2015112114 A | 6/2015 |
| JP | 2015518776 A | 7/2015 |
| JP | 2016515442 A | 5/2016 |
| JP | 2016116863 A | 6/2016 |
| WO | 1988009682 A1 | 12/1988 |
| WO | 0056237 A2 | 9/2000 |
| WO | 02102231 A2 | 12/2002 |
| WO | 2005041748 A2 | 5/2005 |
| WO | 2008049087 A2 | 4/2008 |
| WO | 2011143468 A2 | 11/2011 |
| WO | 2013049601 A2 | 4/2013 |
| WO | 2013052919 A2 | 4/2013 |
| WO | 2013154776 A2 | 10/2013 |
| WO | 2014168987 A1 | 10/2014 |
| WO | 2015049784 A1 | 4/2015 |
| WO | 2016183337 A2 | 11/2016 |
| WO | 2016210437 A1 | 12/2016 |
| WO | 2017024306 A1 | 2/2017 |
| WO | 2017087549 A1 | 5/2017 |
| WO | 2018106569 A1 | 6/2018 |
| WO | 2018129133 A1 | 7/2018 |
| WO | 2019095020 A1 | 5/2019 |
| WO | 2019138321 A1 | 7/2019 |

OTHER PUBLICATIONS

Seror, O., "Ablative therapies: Advantages and disadvantages of radiofrequency, cryotherapy, microwave and electroporation methods, or how to choose the right method for an individual patient?" Diagnostic and Interventional Imaging 96:617-624 (Apr. 2015).

Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.

Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.

Co-Pending U.S. Appl. No. 14/578,807, filed Dec. 22, 2014, 21 pages.

Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.

Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.

Extended European Search Report for Application No. EP17168513.4 dated Sep. 18, 2017, 11 pages.

Extended European Search Report for European Application No. 15201723.2, dated May 11, 2016, 07 Pages.

Extended European Search Report for European Application No. 17168393.1 dated Dec. 15, 2017, 12 Pages.

Extended European Search Report for European Application No. 17168518.3, dated Sep. 20, 2017, 9 Pages.

Extended European Search Report for European Application No. 17173893.3, dated Nov. 6, 2017, 8 Pages.

Extended European Search Report for European Application No. 17201434.2, dated Feb. 1, 2018, 10 Pages.

Extended European Search Report for European Application No. 17205876.0, dated Jun. 1, 2018, 13 Pages.

Extended European Search Report for European Application No. 19177365.4, dated Nov. 8, 2019, 07 Pages.

Extended European Search Report for European Application No. 19183327.6, dated Nov. 21, 2019, 8 Pages.

Extended European Search Report for European Application No. 20153872.5, dated May 7, 2020, 9 Pages.

Extended European Search Report for European Application No. 20195648.9, dated Feb. 12, 2021, 8 Pages.

Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.

Haines D.E., et al., "The Promise of Pulsed Field Ablation," Dec. 2019, vol. 19, No. 12, 10 pages.

Honarbakhsh S., et al., "Radiofrequency Balloon Catheter Ablation for Paroxysmal Atrial Fibrillation, Radiance Study—a UK experience," EP Europace, Oct. 2017, vol. 19, No. 1, p. i21, 3 Pages.

International Search Report and Written Opinion for International Application No. PCT/IB2019/052313, dated Jul. 22, 2019, 8 Pages.

International Search Report and Written Opinion for International Application No. PCT/IB2019/056381, dated Dec. 17, 2019, 10 pages.

International Search Report and Written Opinion for International Application No. PCT/IB2019/057743, dated Dec. 6, 2019, 16 Pages.

International Search Report and Written Opinion issued in corresponding International Application No. PCT/IB2019/057742, dated Nov. 28, 2019, 18 Pages.

Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.

Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.

Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.

Partial European Search Report for European Application No. 17168393.1 dated Sep. 13, 2017, 13 Pages.

Partial European Search Report for European Application No. 17205876.0, dated Feb. 22, 2018, 10 Pages.

Reddy V.Y., et al., "Balloon Catheter Ablation to Treat Paroxysmal Atrial Fibrillation: What is the Level of Pulmonary Venous Isolation?," Heart Rhythm, Mar. 2008, vol. 5, No. 3, pp. 353-360, 3 Pages.

Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.

Youtube:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QKMWJME].

Youtube: "New Interface TactiCath Contact Force Ablation Catheter," Nov. 26, 2013, 1 Pages, [Retrieved on Nov. 19, 2020], Retrieved from URL: https: /Avww.youtube.com/watch?v=aYvYO8Hpylg].

(56) References Cited

OTHER PUBLICATIONS

Extended European Search Report dated Sep. 30, 2022, from corresponding European Application No. 22151293.2.

* cited by examiner

INTRAVASCULAR BALLOON WITH SLIDABLE CENTRAL IRRIGATION TUBE

CROSS REFERENCE TO RELATED APPLICATIONS

The present application claims priority to prior filed U.S. Provisional Application No. 63/137,270 filed on Jan. 14, 2021 which is hereby incorporated by reference as set forth in full herein.

FIELD

The present invention relates to medical instruments, and in particular balloon catheters.

BACKGROUND

Some intravascular treatments utilize balloon catheters having an inflatable balloon near a distal end of the catheter. There are a variety of balloon catheter designs usable for various purposes where, generally, the balloon is collapsible to traverse vasculature and expandable within a blood vessel and/or heart. Typically, the balloon is inflated and deflated by pumping a fluid (e.g. saline solution) through an inflation tube and/or lumen of the catheter. Some balloon catheters can further provide irrigation through pores in the balloon, where such porous balloons are referred to herein as an "irrigation balloon".

Some irrigation balloons include electrodes for sensing and/or ablation such as described in U.S. Patent Application Publication 2020/0155226, U.S. Patent Application Publication 2019/0298441, and U.S. Pat. No. 7,410,486, each incorporated by reference herein. Such irrigation balloons can be used in treatments involving catheter ablation of cardiac arrhythmias. The irrigation balloon catheter can provide fluid for controlling temperature of blood and/or tissue during ablation, for instance.

Generally, larger volume balloons can require longer inflation and deflation times compared to smaller volume balloons. In some irrigation balloons, pores in the balloon can allow fluidic ingress into the irrigation balloon absent negative pressure, which may allow the balloon to at least partially expand when deflated. Some irrigation balloons include a mechanism within and/or attached to the irrigation balloon to facilitate inflation and/or deflation of the irrigation balloon. See, for example, U.S. Patent Application Publication 2018/0140807, U.S. Patent Application Publication 2018/0161093, U.S. Patent Application Publication 2019/0059818, U.S. Patent Application Publication 2019/0201669, U.S. Patent Application Publication 2019/0217065, U.S. Patent Application Publication 2020/0147295, and U.S. Pat. No. 9,907,610, each incorporated by reference herein. Such irrigation balloons can also include electrodes for sensing and/or ablation.

SUMMARY

Examples presented herein generally include a balloon catheter having a central tube that is configured to both structurally support and inflate a balloon membrane, methods of use, and methods of construction of the same. The central tube has a lumen and inflation ports that provide a flow path for inflating the balloon. The central tube allows the balloon membrane to be inflated without requiring an additional inflation tube inserted under the balloon membrane. The lumen of the central tube is obstructed by a distal end piece, nose piece, or other structure to prevent fluid from exiting a distal end of the central tube. The central tube is configured such that, during inflation, inflation media is allowed to pass through an elongated shaft of the catheter, into a proximal open end of the central tube, and through the inflation ports into the balloon. The central tube can be configured to slide longitudinally in relation to the shaft to longitudinally elongate and/or truncate the balloon. The balloon catheter can include various sensors and electrodes to function with cardiac mapping and/or ablation systems.

An example balloon catheter can include an elongated shaft, an inflatable balloon, a central tube, and an end plug. The elongated shaft extends along a longitudinal axis of the balloon catheter. The inflatable balloon can be disposed approximate a distal end of the shaft. The end plug can be disposed approximate a distal end of the central tube.

The inflatable balloon can have an interior configured to receive an inflation medium to inflate the inflatable balloon. A distal end of the inflatable balloon can be affixed to the central tube. A proximal end of the inflatable balloon being affixed to the shaft.

The central tube can extend along the longitudinal axis. At least a portion of the central tube can be positioned within the inflatable balloon, provide structural support for the inflatable balloon, include inflation ports, and have a central lumen in fluidic communication with the inflation ports. The central tube can be coupled to the distal end of the shaft so that the central tube is movable to extend and/or contract the inflatable balloon in length in relation to the longitudinal axis.

The central lumen and inflation ports can provide a flow path between the inflatable balloon interior and the shaft to allow the inflation medium to pass from the shaft into the interior of the inflatable balloon. The central lumen can include an opening positioned in a proximal direction in relation to the inflation ports and in fluidic communication with the shaft to allow the inflation medium to travel from the shaft into the central lumen.

The central lumen can be obstructed by an obstruction at a position distal to the inflation ports so that inflation medium is inhibited from moving through the central lumen distal of the obstruction. The end plug can be configured to prevent loss of fluid through the distal end of the tube. The end plug and the obstruction can be one in the same.

The balloon catheter can further include a collapsing set of splines and a membrane affixed to the splines. The splines can be made at least partially from a shape-memory material having a collapsed pre-formed shape that collapses the inflatable balloon. The inflatable balloon can include the membrane.

The balloon catheter can further include an elastic element and a puller-wire. The elastic element can be coupled to the central tube and shaft. The elastic element can be configured to self-elongate thereby sliding the central tube distally in relation to the shaft and extending the inflatable balloon in length in relation to the longitudinal axis. The puller-wire can be connected to the central tube, extend through the shaft, and be accessible for retraction during treatment so that retraction of the puller-wire compresses the elastic element in the direction of the longitudinal axis thereby sliding the central tube in relation to the shaft and contracting the inflatable balloon in length in relation to the longitudinal axis.

The balloon catheter can further include a fluid impermeable seal between the central tube and the shaft, disposed over the central tube and within the shaft.

The balloon catheter can further include a navigation sensor disposed within the central lumen. The navigation sensor can be a three axis inductive sensor. The navigation sensor can be positioned in a distal direction in relation to the inflation ports. The balloon catheter can further include a sensor wire in electrical communication with the navigation sensor and extending through at least a portion of the central lumen.

The balloon catheter can further include irrigation ports disposed on or over the inflatable balloon. The balloon catheter can be configured to irrigate via the irrigation ports. The irrigation ports can be positioned on the inflatable balloon so that the flow path extends from the shaft, through the central lumen, through the inflation ports, through the interior of the inflatable balloon, and through the irrigation ports. The balloon catheter can further include a plurality of electrodes disposed on the outer surface of the inflatable balloon and one or more wires connected to each of the plurality of electrodes. Each wire can extend through the shaft.

As an alternative to the inflation balloon being also an irrigation balloon, the balloon catheter can include an irrigation balloon comprising irrigation ports and being disposed over the inflatable balloon so that inflation of the inflatable balloon at least partially inflates the irrigation balloon. The balloon catheter can include a chamber between the irrigation balloon and the inflatable balloon that is fluidically separate from the interior of the inflatable balloon and in fluidic communication with the irrigation ports. The balloon catheter can further include a plurality of electrodes disposed on the outer surface of the irrigation balloon and one or more wires connected to each of the plurality of electrodes, each wire extending through the shaft.

An example method can include some or all of the following steps that can be executed in various orders, and the method can include additional steps not listed. The method can include inflating an inflatable balloon of a balloon catheter through a flow path that traverses an elongated shaft of the balloon catheter, a central lumen of a central tube positioned within the inflatable balloon, inflation ports of the central tube, and an interior of the inflatable balloon. The method can include structurally supporting the inflatable balloon along a longitudinal axis of the balloon catheter with the central tube, the central tube being aligned with the longitudinal axis so that at least a portion of the central tube is positioned within the inflatable balloon.

The method can include sliding the central tube in relation to the shaft to thereby extend and/or contract the inflatable balloon in length in relation to the longitudinal axis.

The method can include collapsing a set of splines made at least partially from a shape-memory material having a collapsed pre-formed shape that collapses the inflatable balloon.

The method can include extending the inflatable balloon in length in relation to the longitudinal axis by allowing an elastic element coupled to the central tube and shaft to self-elongate thereby sliding the central tube longitudinally in relation to the shaft. The method can include retracting the inflatable balloon in length in relation to the longitudinal axis by retracting a puller-wire connected to the central tube and extending through the shaft thereby compressing the elastic element in the direction of the longitudinal axis and sliding the central tube longitudinally in relation to the shaft.

The method can include inhibiting, by a distal end piece of the catheter, inflation medium from exiting a distal end of the central lumen.

The method can include traversing, with the flow path, an opening in the central tube, the opening being in fluidic communication with the central lumen, in fluidic communication with the shaft, and positioned in a proximal direction from the inflation ports.

The method can include determining a position of the inflatable balloon based on electrical signals provided by a navigation sensor disposed within the central lumen. The navigation sensor can be a three axis inductive sensor.

The method can include positioning the navigation sensor in a distal direction in relation to the inflation ports.

The method can include receiving the electrical signals via a sensor wire in electrical communication with the navigation sensor and extending through at least a portion of the central lumen.

The method can include irrigating through irrigation ports disposed on or over the inflatable balloon.

The method can include positioning the irrigation ports on the inflatable balloon so that the flow path extends from the shaft, through the central lumen, through the inflation ports, through the interior of the inflatable balloon, and through the irrigation ports. The method can include receiving and/or providing electrical signals to a plurality of electrodes disposed on the outer surface of the inflatable balloon via one or more wires connected to each of the plurality of electrodes, each wire extending through the shaft.

As an alternative to positioning irrigation ports on the inflatable balloon, the method can include disposing the irrigation ports on an irrigation balloon. The method can include disposing the irrigation balloon over the inflatable balloon. The method can include inflating the inflatable balloon to at least partially inflate the irrigation balloon. The method can include fluidically separating the irrigation balloon and the interior of the inflatable balloon with a chamber therebetween. The method can include fluidically communicating the chamber with the irrigation ports. The method can include receiving and/or providing electrical signals to a plurality of electrodes disposed on the outer surface of the irrigation balloon via one or more wires connected to each of the plurality of electrodes, each wire extending through the shaft.

Another example method can include some or all of the following steps that can be executed in various orders, and the method can include additional steps not listed. The method can include coupling a central tube to a distal end of an elongated catheter shaft so that the central tube has a central lumen in fluidic communication with the catheter shaft and so that inflation ports on the central tube are in fluidic communication with the central lumen and thereby the shaft. The method can include affixing an inflatable balloon approximate a distal end of the shaft and over at least a portion of the central tube so that the inflation ports are positioned within an interior of the inflatable balloon and the inflatable balloon is configured to receive inflation medium through a flow path that extends through the shaft, through the central lumen, and through the inflation ports into the interior of the balloon to inflate the inflatable balloon.

The method can include coupling the central tube to the distal end of the shaft so that the central tube is movable to extend and/or contract the inflatable balloon in length in relation to the longitudinal axis.

The method can include affixing a distal end of the inflatable balloon to the central tube. The method can include affixing a proximal end of the inflatable balloon to the shaft.

The method can include forming a set of splines made at least partially from a shape-memory material into a collapsed pre-formed shape. The method can include affixing the set of splines to the balloon catheter in relation to the inflatable balloon such that moving the splines to the collapsed pre-formed shape collapses the inflatable balloon.

The method can include coupling an elastic element to the central tube and shaft such the elastic element is configured to self-elongate and cause the central tube to slide in relation to the shaft thereby extending the inflatable balloon in length in relation to the longitudinal axis. The method can include connecting a puller-wire to the central tube. The method can include extending the puller-wire through the shaft so that the puller-wire is accessible for retraction during treatment so that retraction of the puller-wire compresses the elastic element in the direction of the longitudinal axis thereby sliding the central tube proximally in relation to the shaft and contracting the inflatable balloon in length in relation to the longitudinal axis.

The method can include obstructing the central lumen at a position distal to the inflation ports so that inflation medium is inhibited from moving through the central lumen distal of the obstruction.

The method can include positioning an opening on the central tube to the central lumen in a proximal direction in relation to the inflation ports so that the opening is in fluidic communication with the shaft to allow the inflation medium to travel from the shaft into the central lumen.

The method can include disposing a fluid impermeable seal between the central tube and the shaft so that the fluid impermeable seal is over the central tube and within the shaft.

The method can include affixing a navigation sensor within the central lumen. The navigation sensor can be a three axis inductive sensor. The method can include affixing the navigation sensor in a distal direction in relation to the inflation ports. The method can include electrically connecting a sensor wire to the navigation sensor. The method can include extending the sensor wire through at least a portion of the central lumen.

The method can include configuring the balloon catheter to irrigate through irrigation ports disposed on or over the inflatable balloon. The method can include configuring the inflatable balloon to irrigate through the irrigation ports.

The method can include positioning the irrigation ports on the inflatable balloon so that the flow path extends from the shaft, through the central lumen, through the inflation ports, through the interior of the inflatable balloon, and through the irrigation ports. The method can include disposing a plurality of electrodes on the outer surface of the inflatable balloon. The method can include electrically connecting one or more wires to each of the plurality of electrodes. The method can include extending each wire through the shaft.

As an alternative to positioning irrigation ports on the inflatable balloon, the method can include disposing an irrigation balloon having irrigation ports over the inflatable balloon so that inflation of the inflatable balloon at least partially inflates the irrigation balloon. The method can include forming a chamber between the irrigation balloon and the inflatable balloon that is fluidically separate from the interior of the inflatable balloon and in fluidic communication with the irrigation ports. The method can include disposing a plurality of electrodes on the outer surface of the irrigation balloon. The method can include electrically connecting one or more wires to each of the plurality of electrodes. The method can include extending each wire through the shaft.

Another example catheter can include an elongated shaft, an inflatable balloon, a central tube, and a distal end piece. The elongated shaft can extend from a proximal end to a distal end along a longitudinal axis of the balloon catheter. The inflatable balloon can be disposed approximate the distal end of the shaft. The inflatable balloon can include an interior configured to receive an inflation medium to inflate the inflatable balloon to a first expanded volume defined by a truncated cone having its base connected to a semi-toroid. The central tube can extend along the longitudinal axis. At least a portion of the central tube can be positioned within the inflatable balloon, provide structural support for the inflatable balloon, include inflation ports, and have a central lumen in fluidic communication with the inflation ports. The central lumen and inflation ports can provide a flow path between the inflatable balloon interior and the shaft to allow the inflation medium to pass from the shaft into the interior of the inflatable balloon. The central tube can be configured to move along the longitudinal axis to change the first expanded volume to a second expanded volume defined substantially by two truncated cones connected at their respective bases.

The distal end piece can include an end plug (or nose piece) to prevent loss of fluid through the central tube.

This example catheter can further include features and structures of the above example catheter. This example catheter can be constructed and/or used according to the above example methods.

Steps of the above example methods can be combined in a single method.

DETAILED DESCRIPTION

Figure 1A:
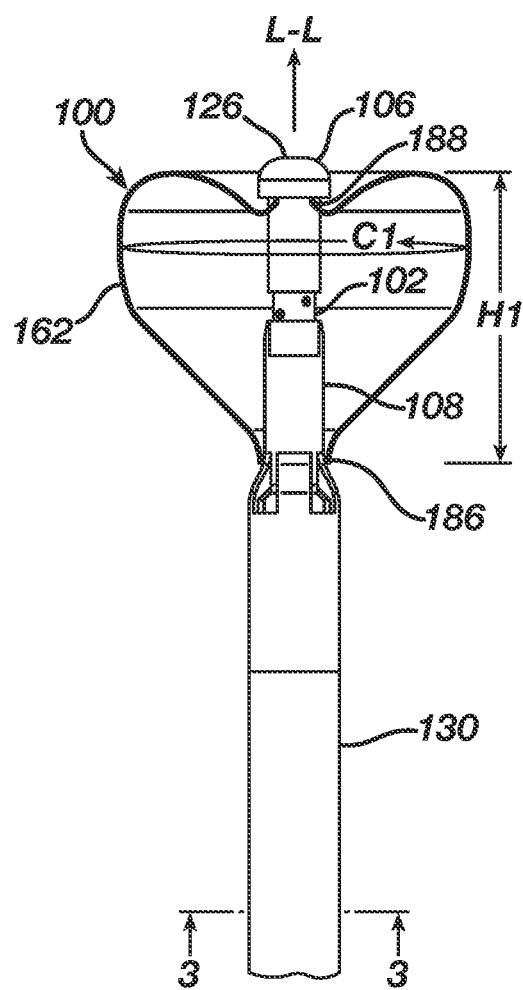
FIG. 1A is an illustration of a distal portion of an example irrigation balloon catheter in a radially expanded, longitudinally retracted state (first inflated state) according to aspects of the present invention.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

As used herein, the terms "patient," "host," "user," and "subject" refer to any human or animal subject and are not intended to limit the systems or methods to human use, although use of the subject invention in a human patient represents a preferred embodiment.

As used herein, the terms "tubular" and "tube" are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered outer surface, a curved outer surface, and/or a partially flat outer surface without departing from the scope of the present disclosure.

Examples presented herein generally include a balloon catheter having a central tube that is configured to both structurally support and inflate a balloon membrane. The central tube can have a lumen and sidewall inflation ports that provide a path for inflating the balloon. The lumen of the central tube can be obstructed by a distal end piece, nose piece, or other structure to prevent fluid from exiting a distal end of the central tube. The central tube can be configured such that, during inflation, inflation media is allowed to pass through an elongated shaft of the catheter, into a proximal open end of the central tube, and through the inflation ports into the balloon. The central tube lumen may be configured to accommodate a larger inner diameter compared to an irrigation lumen of a balloon catheter having a separate support tube and irrigation tube. A larger irrigation lumen can potentially reduce overall back pressure and load on a pump supplying fluid to the balloon. The central tube can further be configured to slide longitudinally in relation to the shaft to longitudinally elongate and/or retract the balloon.

The central tube can be attached via the shaft to a luer hub for catheter irrigation. The central tube can be attached to an advancement system within a handle (such as a drive or slider, manually or powered via hydraulic or electrically activated) which an end user (e.g. physician) can use to push the central tube resulting in balloon advancement. Interstitial space around an outer diameter of the central tube can be sealed using a conformal friction seal or bellows or folding sleeve to prevent irrigation at pressure in balloon from entering the proximal section of the catheter including handle. The seal can prevent leaking while allowing advancement of the central tube from the shaft to elongate the balloon. Various types of seals may be suitable for the purpose such as bellows, conformal, O-ring, etc. Balloon membrane can be made from polyethylene terephthalate (PET), polyurethane, polyether block amide, or any other suitable material A navigation sensor (e.g. three axis sensor, "TAS") can be embedded in the central tube at a position that is distal to the inflation ports. Positioned as such, a sensor wire carrying signals from the navigation sensor can be positioned in the central tube lumen. Positioning of the sensor wire within the central tube lumen can alleviate space constraints within the balloon at a marginal tradeoff of increasing back pressure of inflation fluid. The sensor wire can be brought out of the central tube lumen and sealed in the handle. The sensor wire can be positioned and otherwise configured to provide strain relief to accommodate slack in the handle.

Example catheters presented herein can be modified in several manners as understood by a person skilled in the pertinent art according the teachings herein. Irrigation balloons can include electrodes for sensing and/or ablation such as described in U.S. Patent Application Publication 2020/0155226, U.S. Patent Application Publication 2019/0298441, and U.S. Pat. No. 7,410,486, each incorporated by reference herein. Irrigation balloons can include a mechanism within and/or attached to the irrigation balloon to facilitate inflation and/or deflation of the irrigation balloon and/or telescoping of the central tube such as presented in U.S. Patent Application Publication 2018/0140807, U.S. Patent Application Publication 2018/0161093, U.S. Patent Application Publication 2019/0059818, U.S. Patent Application Publication 2019/0201669, U.S. Patent Application Publication 2019/0217065, U.S. Patent Application Publication 2020/0147295, and U.S. Pat. No. 9,907,610, each incorporated by reference herein. Likewise, example catheters presented herein can include additional components such as navigation sensors, thermocouples, a mechanism for deflecting a distal portion of the catheter shaft, a force sensor, and other compatible electrical and mechanical features. Omission of such features from the figures are solely for the sake of clarity in illustration, and any of the depicted example catheters can be modified to include such features as understood by a person skilled in the pertinent art.

Figure 1B:
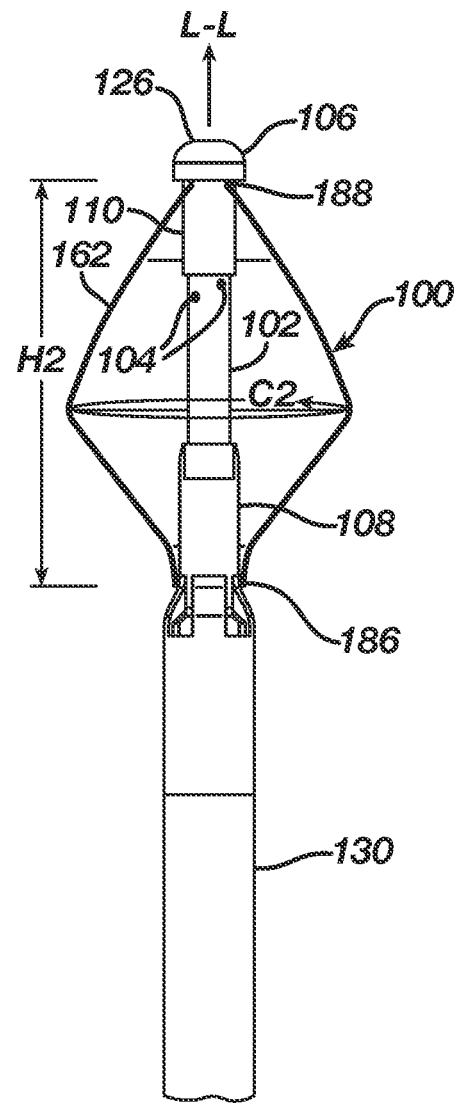
FIG. 1B is an illustration of the distal portion of the irrigation balloon catheter in a radially expanded, longitudinally extended state (second inflated state) according to aspects of the present invention.
Figure 1C:
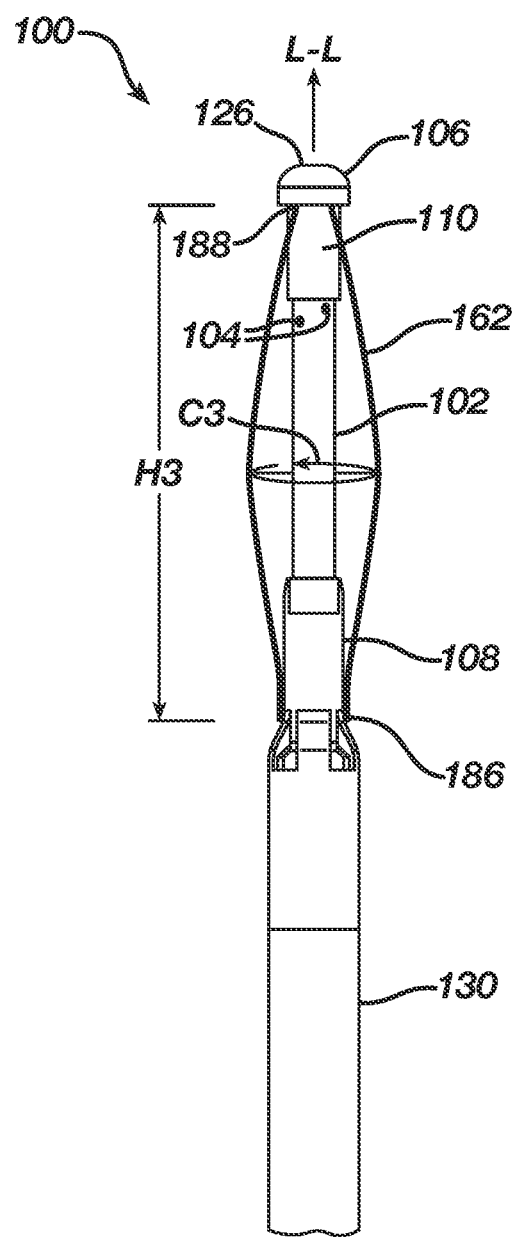
FIG. 1C is an illustration of the distal portion of the irrigation balloon catheter further extended in radially contracted, longitudinally extended state (deflated state) according to aspects of the present invention.

FIGS. 1A through 1C are illustrations of a distal portion of an example balloon catheter 100. The distal portion of the balloon catheter 100 is illustrated in a radially expanded, longitudinally retracted state in FIG. 1A, a longitudinally extended state in FIG. 1B, and in a deflated state in FIG. 1C.

Figure 2A:
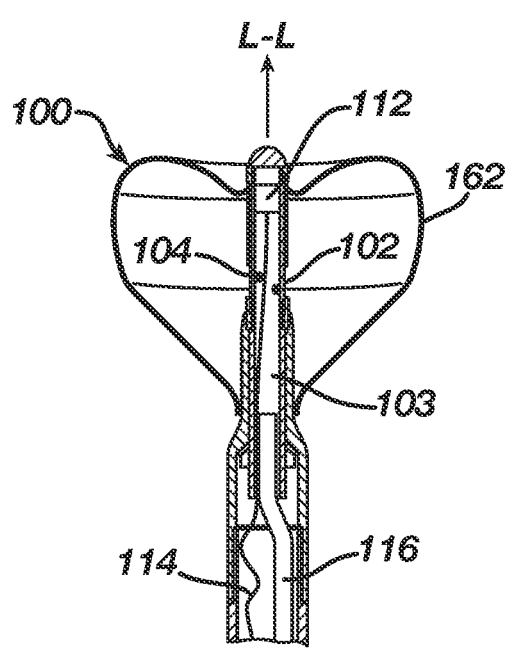
FIGS. 2A and 2B are respectively illustrations of a cross section of the irrigation balloon catheter in the state illustrated in FIGS. 1A and 1B in a plane parallel to the viewing plane of FIGS. 1A and 1B and mid-way through the catheter.
Figure 2B:
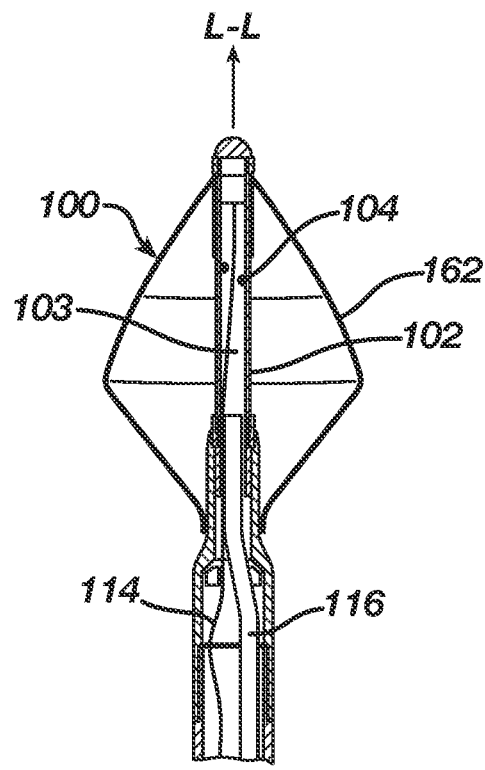

FIGS. 2A and 2B are cross-sectional illustrations of the views of the balloon catheter 100 in FIGS. 1A and 1B respectively.

Referring collectively to FIGS. 1A-1C, 2A, and 2B, the balloon catheter 100 includes an elongated shaft 130, an inflatable balloon 162, a central tube 102, and a distal plug 106. The elongated shaft 130 extends along a longitudinal axis L-L of the balloon catheter 100 and can be manipulated at its proximal end by a handle or other apparatus as understood by a person skilled in the pertinent art. The inflatable balloon 162 is disposed approximate a distal end of the shaft 130. At least a portion of the central tube 102 is positioned within the inflatable balloon 162 The central tube 102 provides structural support for the inflatable balloon 162. The central tube 102 includes inflation ports 104. As better visualized in FIGS. 2A and 2B, the central tube 102 includes a central lumen 103 in fluidic communication with the inflation ports 104. The central lumen 103 and inflation ports 104 provide a flow path between the inflatable balloon interior and the shaft 130 to allow the inflation medium to pass from the shaft 130 into the interior of the inflatable balloon 162. The central tube 102 can move distally along the longitudinal axis L-L to facilitate reshaping of the balloon 162. The distal plug 106 is positioned at a distal end 126 of the catheter 100 to prevent loss of fluid through a distal end of the central tube 102. The distal plug 106 has an atraumatic shape. Alternatively, the distal plug 106 can be positioned within the central tube 102. In such an example, the catheter 100 can have an internal distal end similar to corresponding structures in U.S. 2019/0201669.

FIGS. 1A and 2A illustrate the balloon 162 in a first inflated state inflated to a first expanded volume defined by a truncated cone having its base connected to a semi-toroid. The semi-toroid extends radially and distally from a distal end 188 of the balloon 162 that is attached near a distal end of the central tube 102; the semi-toroid then curves proximally to a first circumference C1 that is a maximum circumference of the balloon 162 in the illustrated shape. The truncated cone has an apex at a proximal end 186 of the balloon 162 that is attached to the shaft 130; the truncated cone extends radially and distally from the apex to meet the semi-toroid at the maximum circumference C1. The balloon 162 has a first longitudinal dimension, or first height H1, measured from the proximal end 186 of the balloon 162 to the distal plug 106.

FIGS. 1B and 2B illustrate the balloon in a second inflated state inflated to a second expanded volume defined substantially by two truncated cones connected at their respective bases. The balloon 162 can be moved from the first inflated state to the second inflated state and vice versa by sliding the central tube 102 distally and proximally in relation to the shaft 130. The second volume can be about equal to the first volume. A distal cone has an apex at a distal end 188 of the balloon 162 and extends radially and proximally to a second maximum circumference C2 of the balloon 162. A proximal cone has an apex at the proximal end 186 of the balloon 162 and extends radially and distally to meet the distal cone at the second circumference C2. The balloon 162 has a second height H2 measured from the proximal end 186 of the balloon 162 to the distal plug 106. The second height H2 is greater than the first height H1 because the central tube 102 is extended distally from the shaft 130 compared to as illustrated in FIGS. 1A and 2A. The second circumference C2 is about equal to or less than the first circumference C1.

FIG. 1C illustrates the balloon 162 in a deflated state deflated to a third volume so that the balloon 162 can be repositioned and/or retracted into a catheter. The third volume is significantly less than both the first and second volumes. The balloon 162 is extended to a third height H3, measured from the proximal end 186 of the balloon 162 to the distal plug 106, that is equal to or greater than the second height H2 illustrated in FIGS. 1B and 2B, preferably greater than the second height H2. When the third height H3 is greater than the second height H2, the central tube 102 is extended distally from the shaft when the balloon is moved from the second inflated state to the deflated state. The balloon 162 has a third maximum circumference C3 that is less than the first circumference C1 and the second circumference C2. To deflate the balloon 162, fluid can be extracted from the interior volume of the balloon 162 into the inflation ports 104, through the central lumen 103 of the central tube 102, and into the shaft 130 to be pumped out of the catheter 100 with a pump or other such apparatus.

In some examples, the maximum height H3 (FIG. 1C) can measure about 45 mm and the minimum height H1 (FIG. 1A) can measure about 38 mm. Heights of about 45 mm to about 38 mm can be useful when performing procedures as illustrated and described in relation to FIG. 8, for instance. The heights H1, H2, H3 can otherwise be dimensioned to meet the needs of an intravascular procedure as understood by a person skilled in the pertinent art according to the teachings herein.

FIGS. 2A and 2B illustrates a TAS 112 positioned within the central tube 102 distal to the inflation ports 104 and a sensor wire 114 connected to the TAS 112 and extending through the central lumen 103.

Figure 3:
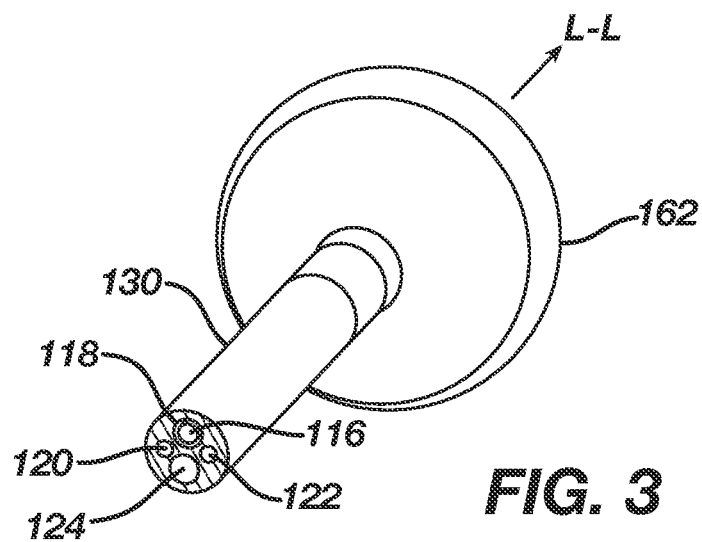
FIG. 3 is an isometric view of the irrigation balloon catheter having cross section through a distal portion of a shaft of the catheter as indicated in FIG. 1A.

FIG. 3 is an isometric view of the catheter 100 where the balloon 162 is in the first inflated state with a cross-sectional view of the shaft 130 as indicated in FIG. 1A.

Referring collectively to FIGS. 2A, 2B, and 3, the catheter 100 includes an interim inflation tube 116 that is stepped into the central tube 102. This stepping can be redesigned so that the inflation tube 116 is an extension of the central tube 102; and/or a lumen of the shaft 130 (e.g. lumen 118 in which the inflation tube 116 is positioned as illustrated) provides functionality of the inflation tube 116. Such alternative designs may further simplify design and construction and improve catheter back pressure.

As illustrated in FIG. 3, the shaft 130 can include multiple lumens 118, 120, 122, 124 to provide several purposes. A first lumen 118 can provide fluid to the balloon as discussed above. Second and third lumens 120, 122 can house pull wires to deflect the balloon 162 away from the longitudinal axis L-L defined by the shaft 130. A fourth lumen 124 can provide a path for wires and cables such as the TAS wire 114, wires to ablation and/or mapping electrodes, etc. The shaft 130 can be modified to include fewer or additional lumens to accommodate alternative structures and functionality as understood by a person skilled in the pertinent art.

Figures 4A, 4B:
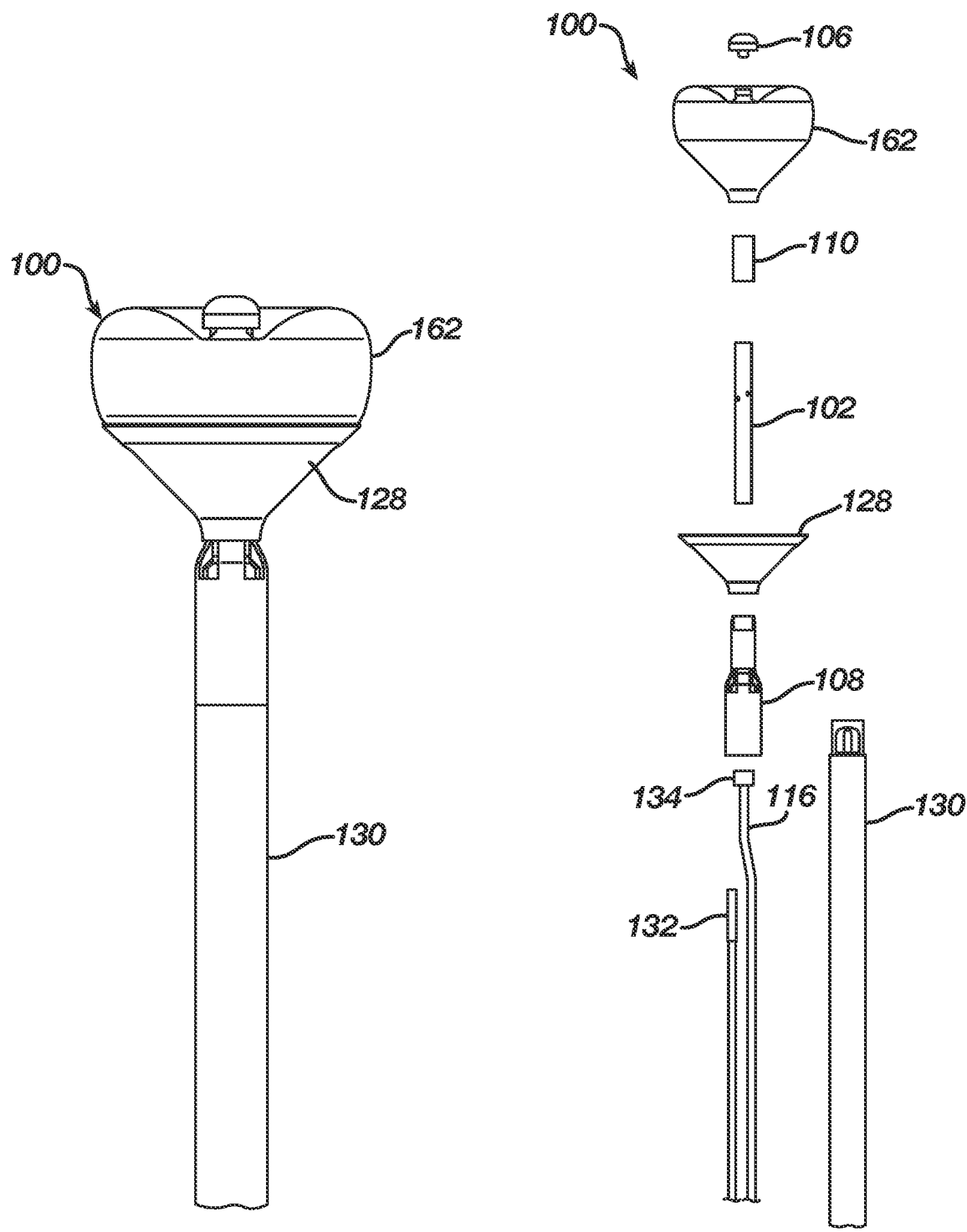
FIG. 4A is an illustration of a distal portion of the example irrigation balloon catheter including an optional expandable conic membrane according to aspects of the present invention.
FIG. 4B is an illustration of an exploded view of the distal portion of the irrigation balloon catheter illustrated in FIG. 4A.

FIGS. 4A and 4B illustrate the catheter 100 including an optional outer membrane 128. FIG. 4B is an exploded view of FIG. 4A. Electrodes (not illustrated) can be mounted over the balloon membrane 162, and wires (not illustrated) to the electrodes can be positioned between the balloon membrane 162 and outer membrane 128 similar to configurations of corresponding structures in U.S. 2020/0155266. The catheter 100 can further include a third membrane configured similarly to corresponding structures in U.S. 2020/0155266.

The catheter 100 can include a navigation sensor 132 positioned in the shaft 130, for instance in the fourth lumen 124 (FIG. 3). The catheter 100 can include an inner ring 110 coupling the central tube 102 to the distal plug 106. The distal end 188 of the balloon 162 can be affixed to the inner ring 110, thereby fixing the distal end of the balloon 162 in relation to the central tube 102. The catheter 100 can include a coupler 108 coupling the proximal end 186 of the balloon 162 to the shaft 130.

The catheter 100 can include a fluid impermeable coupler or seal 134 between the central tube 102 and the shaft 130 so that the fluid impermeable seal 134 is over the central tube and within the shaft. As illustrated, the seal 134 couples the central tube 102 to the inflation tube 116. Alternatively, the shaft 130 can include an inflation lumen sealed to the seal 134 (or similar seal 134 with appropriate configuration) to the central tube 102 so that the inflatable balloon 162 can be inflated directly through the inflation lumen without requiring the inflation tube 116.

Figure 5A:
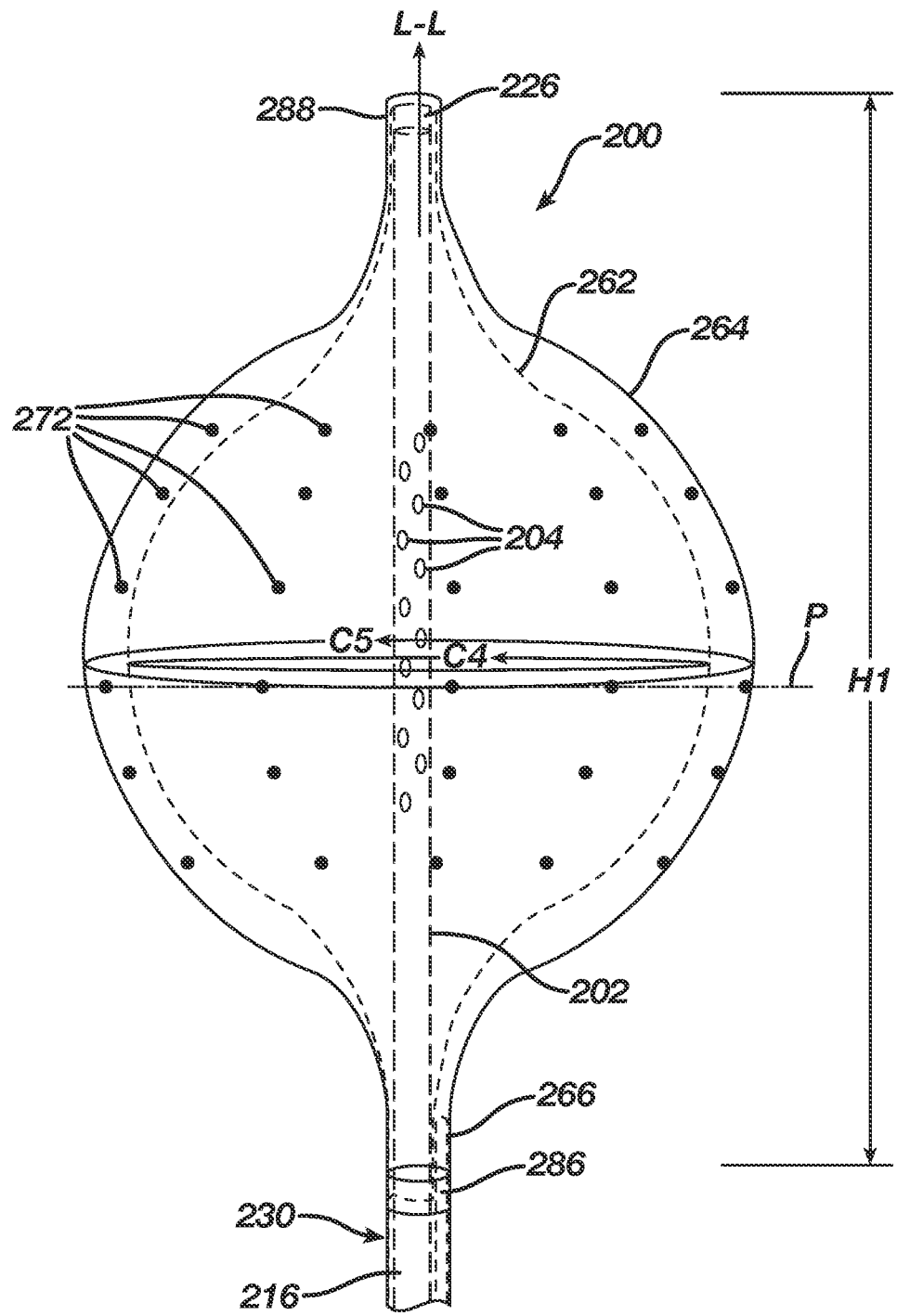
FIG. 5A is an illustration of a distal portion of another example irrigation balloon catheter in a radially expanded, longitudinally retracted state (inflated state) according to aspects of the present invention.
Figure 5B:
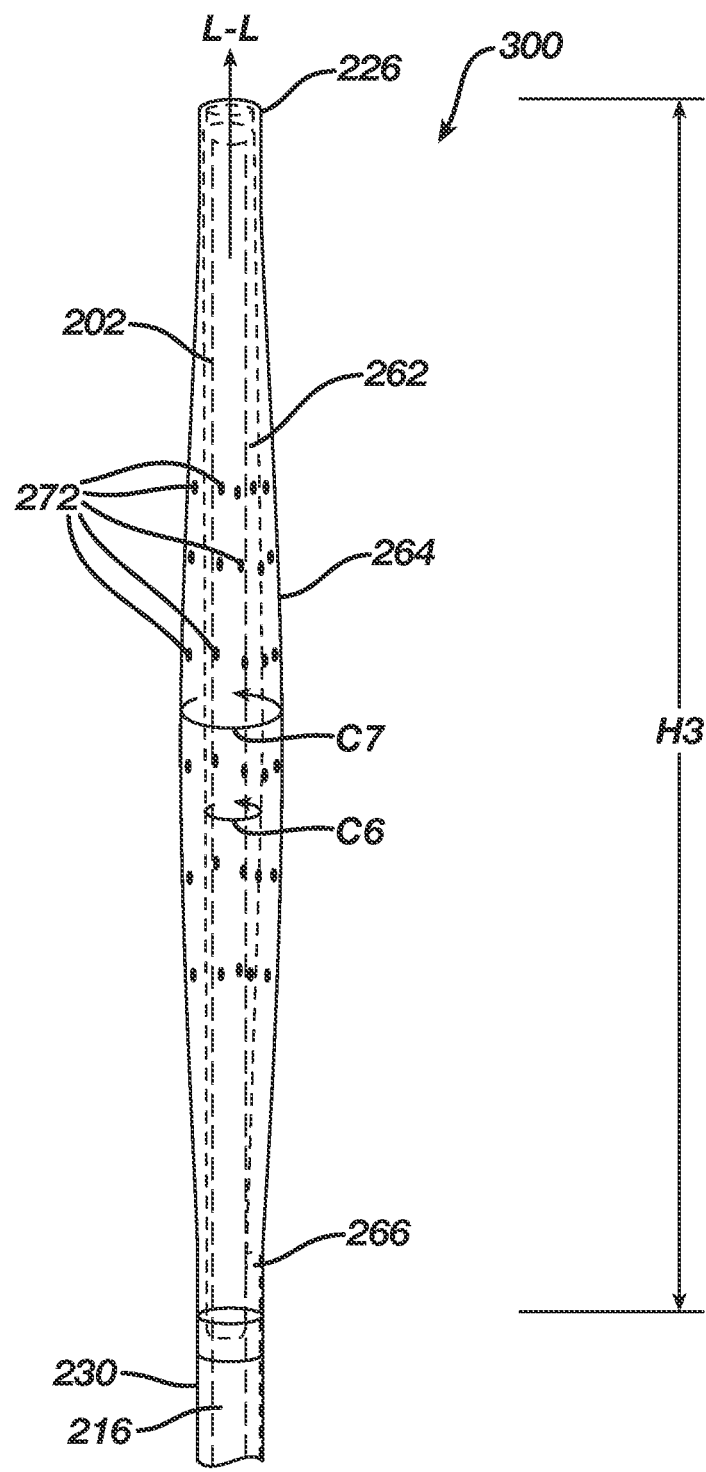
FIG. 5B is an illustration of the distal portion of the irrigation balloon catheter illustrated in FIG. 5A in a radially contracted, longitudinally extended state (deflated state) according to aspects of the present invention.

FIGS. 5A and 5B illustrate an alternative catheter 200 having an irrigation balloon 264 over an inflation balloon 262 and a central tube 202 providing structural support for the balloons 262, 264 and a flow path to inflate the inflation balloon 262. The central tube includes inflation ports 204. The central tube 202 can be configured to inflate and/or deflate the inflation balloon 262 similarly to the central tube 102 illustrated in FIGS. 1A through 4B. The central tube 102 can slide longitudinally in relation to a shaft 230 to adjust a longitudinal dimension, height H1, H3 of the balloons 262, 264. The central tube 202 can be obstructed by a distal plug 106 (FIGS. 1A through 4D) or other obstruction to inhibit fluid from exiting the distal end 226 of the catheter 200.

The irrigation balloon 264 and inner inflation balloon 262 are affixed to each other at a distal balloon end 288 and a proximal balloon end 286 fixed in relation to a catheter shaft 230. An irrigation lumen 266 provides a conduit for irrigation fluid to the irrigation balloon 264. The irrigation balloon 264 includes pores 272 sized and positioned to allow irrigation fluid to exit the interior of the irrigation balloon 264. The non-irrigating inner inflation balloon 262 is impermeable to the irrigation fluid such that no significant amount of irrigation fluid passes from the outer balloon 264 into the inner balloon 262 when negative pressure is applied to deflate the inner balloon 262, meaning any amount of irrigation fluid that may enter the inner balloon 262 during deflation does not significantly affect the resulting volume of the inner balloon 262.

An inflation lumen 216 is fluidically coupled to the central tube 202. The irrigation lumen 266 and inflation lumen 216 are positioned in the shaft 230. The shaft 230, irrigation lumen 266, and inflation lumen 216 can have sufficient length to extend from the treatment site, through vasculature, and outside the patient. The distal portion of the catheter 200 can be placed by manipulation of a proximal portion of the shaft 230. Fluids can be injected into respective proximal openings of the irrigation lumen 266 and inflation lumen 268. The catheter 200 can include an inflation tube similar to the inflation tube 116 illustrated in FIG. 4D. The catheter 200 can include a seal between the central tube 202 and shaft 230 to the irrigation lumen 266 similar to the seal 134 illustrated in FIG. 4D.

Configured as such, the volume of the inner balloon 262 can be deflated more rapidly than an equivalent volume of an irrigation balloon lacking the inner balloon structure 262. This is because, generally, an irrigation balloon includes pores that allow backflow of fluids into the volume of the irrigation balloon when negative pressure is applied to deflate the irrigation balloon.

The catheter 200 can otherwise be manipulated and constructed similar to corresponding catheters in U.S. 2020/0147295.

The irrigation balloon 264 can expand and contract through a range of circumferences during inflation and deflation. The irrigation balloon 264 can have a small circumference C7 when in the deflated state (FIG. 5B) sized so that the irrigation balloon 264 can be retracted into a sheath. The irrigation balloon 264 can have a maximum circumference C5 when in the inflated state (FIG. 5A).

The inner balloon 262 can expand and contract through a range of circumferences during inflation and deflation. The inner balloon 262 can have a small circumference C6 when the catheter 200 is in the deflated state (FIG. 5B) and a larger circumference C4 when the catheter 200 is in an inflated state (FIG. 5A). The circumference C4 of the inner inflation balloon 262 in the inflated state can be sized in relation to the circumference C5 of the irrigation balloon 264 in the inflated state (FIG. 5A) to allow irrigation fluids to pass between the outer surface of the inner balloon 262 and the inner surface of the outer balloon 264 and through the pores 272 at a desired flow rate.

When the balloons 262, 264 are in the inflated state as illustrated in FIG. 5A, the balloons can respectively have circular cross-sectional shapes in plane P. The circular cross-sectional shapes of the balloons 262, 264 can be concentric. The central tube 202 can be concentric with the balloons 262, 264 in the plane P. The balloons 262, 264 can be substantially spherical as illustrated in FIG. 5A or can form inflated shapes similar to those illustrated in FIGS. 1A and 1B.

The central tube 202 can telescope to allow the irrigation balloon 264 and inner balloon 262 to contract and elongate during inflation and deflation. The balloons 262, 264 can have a maximum height H3 when in the deflated state (FIG. 5B) and a minimum height H1 when in the inflated state (FIG. 5A) similar to the example catheter 100 illustrated in FIGS. 1A and 1C.

Figure 6:
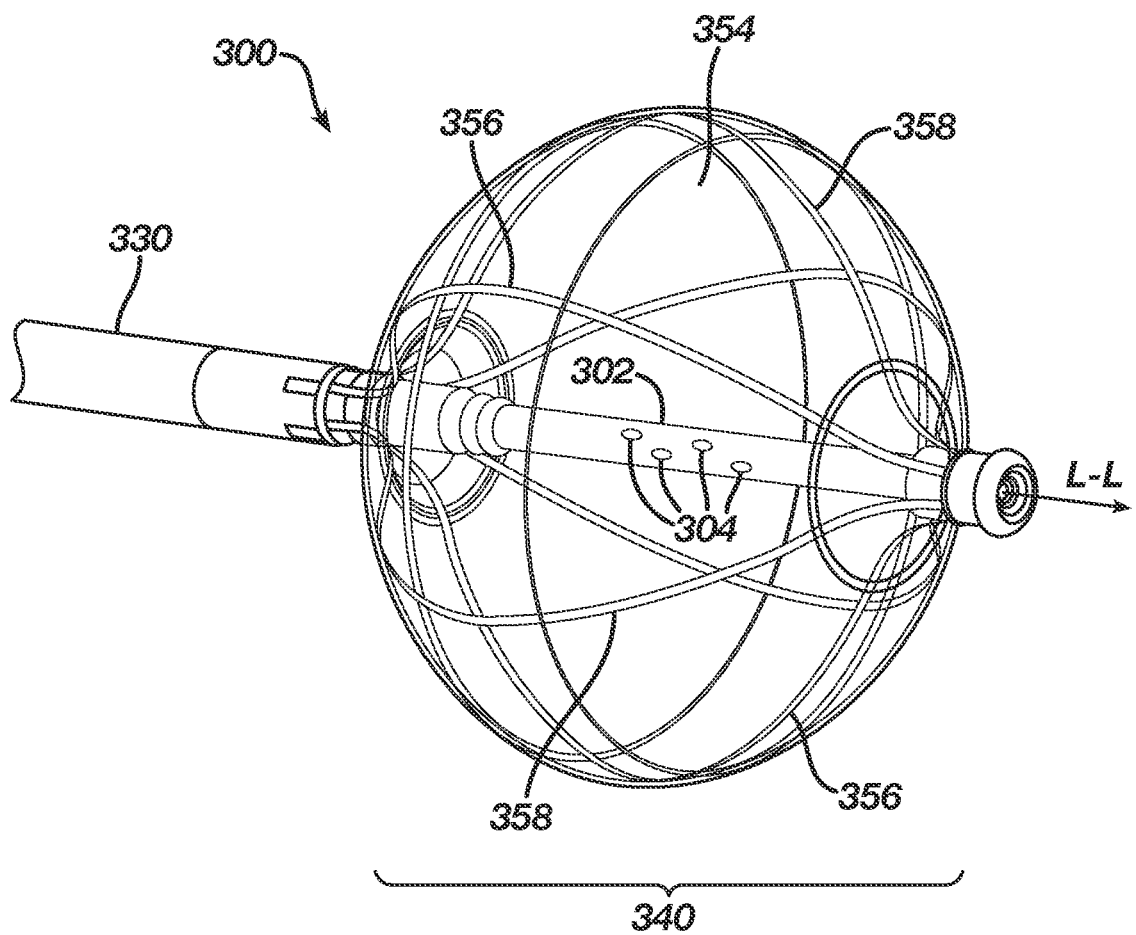
FIG. 6 is an illustration of a distal portion of another example irrigation balloon catheter having collapsible and/or expandable splines according to aspects of the present invention.

FIG. 6 is an illustration of a distal portion of another example balloon catheter 300 having an expanding set of splines 356 and a collapsing set of splines 358. The balloon catheter 300 is illustrated in an inflated state. The catheter 300 includes a central tube 302 having inflation ports 304 configured to inflate a balloon 354 similar to the central tube 102 illustrated in FIGS. 1A through 4B. The central tube 302 can slide longitudinally in relation to a shaft 330 to adjust a longitudinal dimension, height H1, H2, H3 of a balloon 354 similar to as illustrated in FIGS. 1A through 1C. The central tube 302 can be obstructed by a distal plug 106 (FIGS. 1A through 4D) or other obstruction to inhibit fluid from exiting the distal end of the catheter 300.

The catheter 300 includes a balloon assembly 340 including the expanding set of splines 356, the collapsing set of splines 358, the balloon 354, and the central tube 302. The splines can be made at least partially from shape-memory material. The splines 356, 358 are preferably positioned inside the balloon 354, although they can be positioned outside the balloon 354. The splines 356, 358 can be configured to be heated using electrical current provided via suitable wires that run through the catheter's shaft 330. A physician may operate (e.g., activate and deactivate) each of the two sets of splines 356, 358 independently. The splines 356, 358 can be configured similarly to corresponding structures in U.S. 2019/0059818. The catheter 300 can include additional compatible functionality and structures as presented in U.S. 2019/0059818.

The balloon 354 can be expanded by heating of the expanding set of splines 356, and the expanding set of splines 356 can be forced to collapse upon removal of heat. The balloon 354 can be collapsed by heating the collapsing set of splines 358, and the collapsing set of splines 358 can be forced to expand upon removal of the heat. As the balloon 354 expands and collapses, the central tube 302 can slide longitudinally in relation to the shaft to longitudinally elongate and foreshorten the balloon 354. The splines 356, 358 can be affixed so that distal ends of the splines are fixed in relation to the central tube 302 and proximal ends of the splines are fixed in relation to the shaft 330. As the balloon 354 reshapes in response to expansion and/or collapse of the splines 356, 358, the central tube 302 can slide in relation to the shaft 330.

The splines 356, 358 are distributed circumferentially around the inside of the balloon 354. The splines 356, 358 may be assembled in an alternating fashion, e.g., expanding splines 356 placed between two collapsing splines 358, and vice versa. This configuration balances the splines 356 that expand the balloon 354 the splines 358 that collapse and have it back mechanically ready to be easily pulled back into a sheath.

The balloon assembly 340 can include a suitable number of splines, in various suitable arrangements. For example, the number of expanding splines 356 can be different than the number of collapsing splines 358. The balloon assembly 340 can include one or more additional splines that are not made of a shape-memory material. More than two sets of splines can be used. In some examples, the expanding set of splines 356 can be omitted, and pressure from inflation fluid within the balloon 354 can be sufficient to expand the balloon 354. The collapsing set of splines 358 can be activated to collapse the balloon 354 for re-sheathing.

Figure 7A:
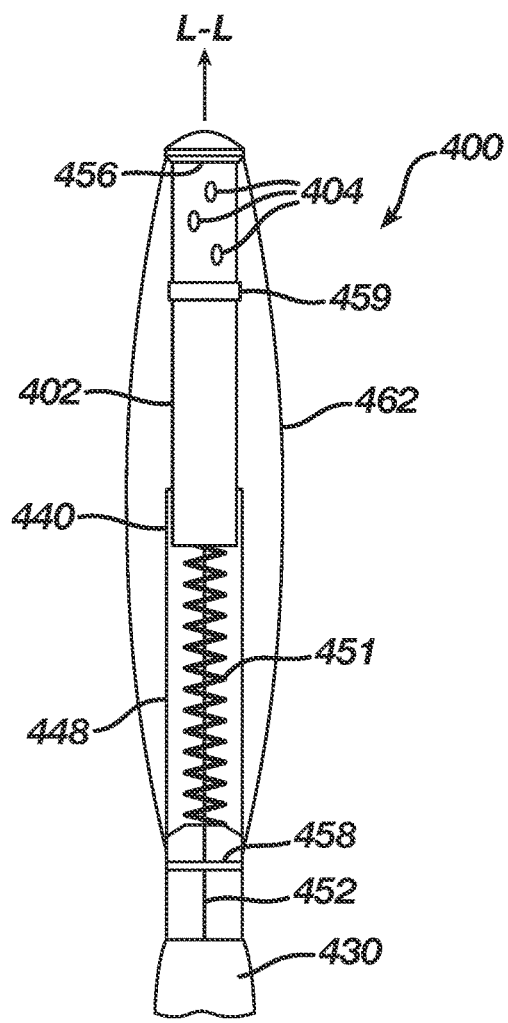
FIG. 7A is an illustration of a distal portion of another example irrigation balloon catheter in a radially contracted, longitudinally extended state (deflated state) and having a self-expandable spring according to aspects of the present invention.
Figure 7B:
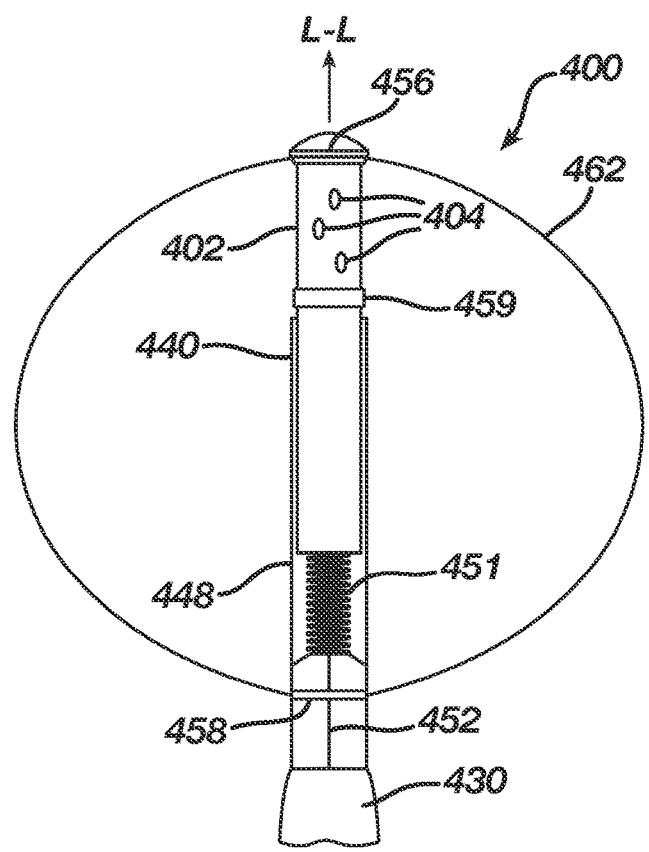
FIG. 7B is an illustration of the distal portion of the irrigation balloon catheter illustrated in FIG. 7A in a radially expanded, longitudinally retracted state (inflated state) according to aspects of the present invention.

FIGS. 7A and 7B are illustrations of a distal portion of another example irrigation balloon catheter 400 having a self-expandable spring 451. FIG. 7A illustrates the distal portion in a radially contracted, longitudinally extended state. FIG. 7B illustrates the distal portion in a radially expanded, longitudinally retracted state. The catheter 400 includes a central tube 402 having inflation ports 404 configured to inflate a balloon 462 similar to the central tube 102 illustrated in FIGS. 1A through 4B. The central tube 402 can slide longitudinally in relation to a shaft 430 to adjust a longitudinal dimension, height H1, H2, H3 of a balloon 462 similar to as illustrated in FIGS. 1A through 1C. The central tube 402 can be obstructed by a distal plug 106 (FIGS. 1A through 4D) or other obstruction to inhibit fluid from exiting the distal end of the catheter 400.

FIG. 7A illustrates a telescopic balloon assembly 440 of the catheter 400 in an elongated state fitted at the distal end of a shaft 430. A proximal section 448 and the central tube 402 are assembled into a two-part structure of the telescopic assembly 440. The proximal section 448 is tubular and shaped to receive the central tube 402. The proximal section 448 is coupled to the catheter shaft 430. The central tube 402 can move telescopically inside the proximal section 448, i.e., its motion is either proximally or distally along the longitudinal axis L-L. The balloon 462 is coupled at its distal end the central tube 402 by a distal anchor 456 and is coupled at its proximal end to the proximal section 448 by a proximal anchor 458.

A puller-wire 452 runs through the shaft 430 and within the two-part telescopic assembly 440 and is connected to the central tube 402. The puller-wire 452 can be operated (e.g., pulled or relaxed) from a handle (not illustrated). The puller-wire 452 can be pulled to cause the central tube 402 to move into the proximal section 448, thereby foreshortening a longitudinal dimension (i.e. height) of the balloon 462 to move the telescopic assembly 440 from the longitudinally extended height illustrated in FIG. 7A to the longitudinally retracted state illustrated in FIG. 7B. A stopper 459 positioned on the central tube 402 can limit the motion of central tube 402 in the proximal direction when the stopper 459 contacts the proximal section 448. The balloon 462 can then be inflated as illustrated in FIG. 7B. The spring 451 can provide a force to cause the telescopic assembly 440 to move from the longitudinally retracted state illustrated in FIG. 7B to the longitudinally extended state illustrated in FIG. 7A when tension on the puller-wire 452 is relaxed.

The catheter 400 can include an inflation tube or inflation lumen similar to the inflation tube 116 and alternative inflation lumens described in relation to the catheter 100 illustrated in FIGS. 1A through 4B. The catheter 400 can include additional compatible functionality and structures as presented in U.S. 2019/0217065.

Figure 8:
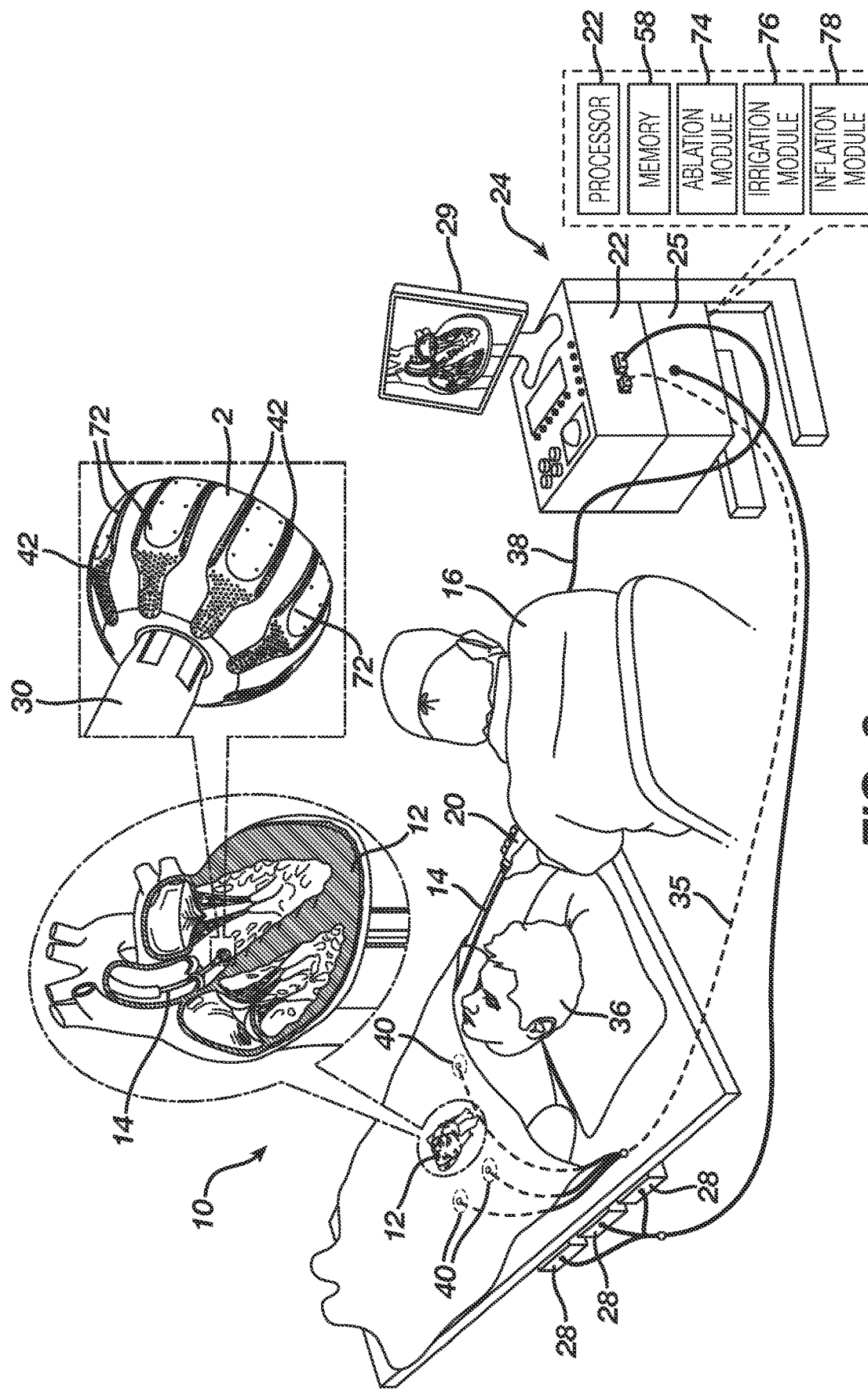
FIG. 8 is an illustration of a system for diagnosis and treatment of a heart of a living patient according to aspects of the present invention.

FIG. 8 is an illustration of a system 10 for diagnosis and/or treatment of a heart 12 of a living patient 36. One commercial product embodying elements of system 10 is available as the CARTO® 3 System, available from Biosense Webster, Inc. located in California, U.S.A.

A balloon catheter 14 can be constructed and function similar to example catheters 100, 200, 300, 400 illustrated and described herein including those described in references incorporated by reference herein, variations thereof, and alternatives thereto as understood by a person skilled in the pertinent art according to the teachings herein. The balloon catheter 14 can further include compatible features of the various catheters 100, 200, 300, 400 illustrated and described herein including those described in the references incorporated by reference herein.

The balloon catheter 14 can be percutaneously inserted by an operator 16 through the patient's vascular system and a shaft 30 of the catheter 14 can be manipulated to position a balloon 2 near a distal end of the balloon catheter 14 in a chamber or vascular structure of the heart 12. The operator 16, who is typically a physician, can inflate the balloon 2 and bring electrodes 42 on the balloon surface into contact with the heart wall, for example, at an ablation target site. The balloon can irrigate through pores 72. The balloon 2 can be configured to inflate via a central tube configured similarly to any of the central tubes 102, 202, 302, 402 illustrated herein, variations thereof, and alternatives thereto as understood by a person skilled in the pertinent art according to the teachings herein. The central tube can telescope to allow the height of the balloon 2 to foreshorten as the balloon 2 is inflated and/or elongate as the balloon 2 is deflated.

Electrical signals measured by the electrodes 42 can be used to prepare electrical activation maps. Electrical activation maps can be prepared, according to methods disclosed in U.S. Pat. Nos. 6,226,542, 6,301,496, and 6,892,091, each incorporated herein by reference.

Areas determined to be abnormal, for example by evaluation of the electrical activation maps, can be ablated by application of thermal energy, e.g., by passage of radiofrequency electrical current through wires in the balloon catheter 14 to one or more electrodes 42 positioned on the balloon 2, which apply the radiofrequency energy to target tissue. The electrodes 42 can be used both for measure electrical signals and apply radiofrequency ablation; alternatively, each process can be performed by different electrodes, potentially on different catheters.

During ablation, energy from the electrical current (alternating in the form of radiofrequency or direct current in bipolar pulse) is absorbed in the tissue, to cause a permanent loss of its electrical excitability. This procedure is typically intended to create non-conducting lesions in the cardiac tissue, which disrupt the abnormal electrical pathway causing the arrhythmia. Such principles can be applied to different heart chambers to diagnose and treat many different types of cardiac arrhythmias.

The catheter 14 can include a handle 20, having suitable controls on the handle to enable the operator 16 to steer, position and orient the distal end of the catheter as desired for ablation and/or diagnosis. To aid the operator 16, the balloon catheter 14 can include position sensors positioned near the distal end of the balloon catheter 14 (e.g. under or near to the balloon 2) that provide signals to a processor 22, located in a console 24. The console 24 can include memory 58 in communication with the processor 22 that when executed by the processor 22 cause the console 24 to perform various functions during treatment. The console 24 can further include an ablation module 74, irrigation module 76, and inflation module 78 that can each respectively include hardware and software (e.g. in memory 58) to execute various functions related to the respective module. The modules 74, 76, 78 can include common hardware and/or software and are included to illustrate various functionality of the console 24. The console 24 can include additional modules not illustrated. The irrigation module 76 and inflation module 78 can be one in the same or separate (e.g. when the catheter 14 includes separate irrigation and inflation balloons).

Ablation energy and electrical signals can be conveyed to and from the heart 12 through the electrodes 42 on the balloon 2 via a cable 38 to the console 24. Pacing signals and other control signals may be conveyed from the console 24 through the cable 38 and the electrodes 42 to the heart 12. This functionality can be controlled by the ablation module 74.

Wire connections 35 link the console 24 with body surface electrodes 40 and other components of a positioning sub-system for measuring location and orientation coordinates of the catheter 14. The processor 22 or another processor may be an element of the positioning subsystem. The electrodes 42 on the balloon 2 and the body surface electrodes 40 may be used to measure tissue impedance at the ablation site as taught in U.S. Pat. No. 7,536,218, incorporated herein by reference.

A temperature sensor, typically a thermocouple or thermistor, may be mounted on or near each of the electrodes 42. An example of the temperature sensor as used in conjunction with the ablation electrode is shown and described in U.S. Patent Publication 2019/0298441 incorporated herein by reference.

The catheter 14 can include a force sensor configured to provide a signal indicative of a magnitude and direction of force applied by a balloon on tissue such as described in U.S. patent application Ser. No. 16/863,815 filed Apr. 30, 2020, titled "Balloon Catheter with Force Sensor", incorporated by reference herein.

The console 24 can include one or more ablation power generators 25 included in, or at least controlled by the ablation module 74. The catheter 14 can be configured to conduct ablative energy to the heart using any known ablation energies or modalities, e.g., radiofrequency energy, electroporation, ultrasound energy, cryogenic energy, and laser-produced light energy. Such methods are disclosed in commonly assigned U.S. Pat. Nos. 6,814,733, 6,997,924, and 7,156,816, and "Theoretical Considerations of Tissue Electroporation With High-Frequency Bipolar Pulses" by Christopher B. Arena, Michael B. Sano, Marissa Nichole Rylander, and Rafael V. Davalos (May 2011), and "Ablative therapies: Advantages and disadvantages of radiofrequency, cryotherapy, microwave and electroporation methods, or how to choose the right method for an individual patient?" by O. Seror (April 2015), each incorporated herein by reference.

The positioning subsystem can include a magnetic position tracking arrangement that determines the position and orientation of the catheter 14 by generating magnetic fields, using magnetic field generators 28, in a predefined working volume and sensing these fields at the catheter, using coils or traces disposed within the catheter, typically proximate to the tip. A positioning subsystem is described in U.S. Pat. Nos. 7,756,576 and 7,536,218, each incorporated herein in their entireties.

The operator 16 may observe and regulate the functions of the catheter 14 via the console 24. The processor 22 can drive a display 29. The processor 22 and associated circuitry of the console 24 can be configured to receive, amplify, filter and digitize signals from the catheter 14, including signals generated by sensors such as electrical, temperature and contact force sensors, and a plurality of location sensing coils or traces located distally in the catheter 14. The digitized signals are received and used by the console 24 and the positioning subsystem to compute the position and orientation of the catheter 14, and to analyze the electrical signals from the electrodes and sensors.

In order to generate electroanatomic maps, the processor 22 can include an electroanatomic map generator, an image registration program, an image or data analysis program and a graphical user interface configured to present graphical information on the display 29.

The system 10 can include other elements, which are not shown in the figures for the sake of simplicity. For example, the system 10 can include an electrocardiogram (ECG) monitor, coupled to receive signals from one or more body surface electrodes, in order to provide an ECG synchronization signal to the console 24. The system 10 can include a reference position sensor, either on an externally applied reference patch attached to the exterior of the subject's body, or on an internally placed catheter, which is inserted into the heart 12 maintained in a fixed position relative to the heart 12. The system 10 can further include pumps and lines for circulating liquids through the catheter 14 for irrigating the treatment site. The system 10 can be configured to receive image data from an external imaging modality, such as an MRI unit, CT, or the like and includes image processors that can be incorporated in or invoked by the processor 22 for generating and displaying images.

What is claimed is:

1. A balloon catheter comprising:
   an elongated shaft extending along a longitudinal axis of the balloon catheter;
   an inflatable balloon disposed approximate a distal end of the elongated shaft and comprising an interior configured to receive an inflation medium to inflate the inflatable balloon;
   a central tube extending along the longitudinal axis,
      at least a portion of the central tube being positioned within the inflatable balloon, providing structural support for the inflatable balloon, comprising inflation ports, and comprising a central lumen in fluidic communication with the inflation ports,
      the central lumen and inflation ports providing a flow path between the inflatable balloon interior and the elongated shaft to allow the inflation medium to pass from the elongated shaft into the interior of the inflatable balloon,
      the central tube being coupled to the distal end of the elongated shaft so that the central tube is movable to extend and/or contract the inflatable balloon in length in relation to the longitudinal axis, and
      a distal end of the inflatable balloon being affixed to the central tube and a proximal end of the inflatable balloon being affixed to the elongated shaft;
   an elastic element, coupled to the central tube and shaft and configured to self-elongate thereby sliding the central tube in relation to the shaft and extending the inflatable balloon in length in relation to the longitudinal axis;
a puller-wire connected to the central tube, extending through the shaft, and configured to be accessible for retraction during treatment so that retraction of the puller-wire compresses the elastic element in along the longitudinal axis thereby sliding the central tube in relation to the shaft and contracting the inflatable balloon in length in relation to the longitudinal axis; and
an end plug disposed approximate a distal end of the central tube and configured to prevent loss of fluid through the distal end of the central tube.

2. The balloon catheter of claim 1, further comprising:
a collapsing set of splines made at least partially from a shape-memory material having a collapsed pre-formed shape that collapses the inflatable balloon; and
a membrane affixed to the splines.

3. The balloon catheter of claim 1,
the central lumen comprising an obstruction at a position distal to the inflation ports so that inflation medium is inhibited from moving through the central lumen distal of the obstruction,
the central lumen comprising an opening positioned in a proximal direction in relation to the inflation ports and in fluidic communication with the shaft to allow the inflation medium to travel from the shaft into the central lumen.

4. The balloon catheter of claim 1, further comprising:
a navigation sensor disposed within the central lumen, the navigation sensor being a three axis inductive sensor, and the navigation sensor being positioned in a distal direction in relation to the inflation ports.

5. The balloon catheter of claim 1, further comprising:
irrigation ports positioned on the inflatable balloon so that the flow path extends from the shaft, through the central lumen, through the inflation ports, through the interior of the inflatable balloon, and through the irrigation ports;
a plurality of electrodes disposed on an outer surface of the inflatable balloon; and
one or more wires connected to each of the plurality of electrodes, each wire extending through the shaft.

6. The balloon catheter of claim 1, further comprising:
an irrigation balloon comprising irrigation ports and being disposed over the inflatable balloon so that inflation of the inflatable balloon at least partially inflates the irrigation balloon and so that the balloon catheter is configured to irrigate via the irrigation ports; and
a chamber between the irrigation balloon and the inflatable balloon that is fluidically separate from the interior of the inflatable balloon and in fluidic communication with the irrigation ports;
a plurality of electrodes disposed on an outer surface of the irrigation balloon; and
one or more wires connected to each of the plurality of electrodes, each wire extending through the shaft.

7. A catheter comprising:
an elongated shaft extending along a longitudinal axis of the catheter;
an inflatable balloon disposed approximate a distal end of the elongated shaft and comprising an interior configured to receive an inflation medium to inflate the inflatable balloon to a first expanded volume defined by a truncated cone having its base connected to a semitoroid;
a central tube extending along the longitudinal axis,
at least a portion of the central tube being positioned within the inflatable balloon, providing structural support for the inflatable balloon, comprising inflation ports, and comprising a central lumen in fluidic communication with the inflation ports,
the central lumen and inflation ports providing a flow path between the inflatable balloon interior and the elongated shaft to allow the inflation medium to pass from the elongated shaft into the interior of the inflatable balloon,
the central tube being configured to move distally along the longitudinal axis to change the first expanded volume to a second expanded volume defined substantially by two truncated cones connected at their respective bases;
an elastic element, coupled to the central tube and shaft and configured to self-elongate thereby sliding the central tube in relation to the shaft and extending the inflatable balloon in length in relation to the longitudinal axis;
a puller-wire connected to the central tube, extending through the shaft, and configured to be accessible for retraction during treatment so that retraction of the puller-wire compresses the elastic element along the longitudinal axis thereby sliding the central tube in relation to the shaft and contracting the inflatable balloon in length in relation to the longitudinal axis; and
a distal plug positioned to prevent loss of fluid through a distal end of the central tube.

8. The catheter of claim 7, a distal end of the inflatable balloon being affixed to the central tube and a proximal end of the inflatable balloon being affixed to the shaft.

9. The catheter of claim 7, further comprising:
a collapsing set of splines made at least partially from a shape-memory material having a collapsed pre-formed shape that collapses the inflatable balloon; and
a membrane affixed to the splines.

10. The catheter of claim 7, the central lumen comprising an opening positioned in a proximal direction in relation to the inflation ports and in fluidic communication with the shaft to allow the inflation medium to travel from the shaft into the central lumen.

11. The catheter of claim 7, further comprising:
irrigation ports disposed on the inflatable balloon so that the flow path extends from the shaft, through the central lumen, through the inflation ports, through the interior of the inflatable balloon, and through the irrigation ports, the catheter being configured to irrigate via the irrigation ports;
a plurality of electrodes disposed on an outer surface of the inflatable balloon; and
one or more wires connected to each of the plurality of electrodes, each wire extending through the shaft.

12. The catheter of claim 7, further comprising:
an irrigation balloon comprising irrigation ports and being disposed over the inflatable balloon so that inflation of the inflatable balloon at least partially inflates the irrigation balloon, the catheter being configured to irrigate via the irrigation ports;
a chamber between the irrigation balloon and the inflatable balloon that is fluidically separate from the interior of the inflatable balloon and in fluidic communication with the irrigation ports;
a plurality of electrodes disposed on an outer surface of the irrigation balloon; and one or more wires connected to each of the plurality of electrodes, each wire extending through the shaft.

13. A method comprising:
inflating an inflatable balloon of a balloon catheter through a flow path that traverses an elongated shaft of the balloon catheter, a central lumen of a central tube positioned within the inflatable balloon, inflation ports of the central tube, and an interior of the inflatable balloon;
structurally supporting the inflatable balloon along a longitudinal axis of the balloon catheter with the central tube, the central tube being aligned with the longitudinal axis so that at least a portion of the central tube is positioned within the inflatable balloon;
extending the inflatable balloon in length in relation to the longitudinal axis by allowing an elastic element coupled to the central tube and shaft to self-elongate thereby sliding the central tube longitudinally in relation to the shaft; and
contracting the inflatable balloon in length in relation to the longitudinal axis by retracting a puller-wire connected to the central tube and extending through the shaft thereby compressing the elastic element along the longitudinal axis and sliding the central tube longitudinally in relation to the shaft.

14. The method of claim 13, further comprising:
collapsing a set of splines made at least partially from a shape-memory material having a collapsed pre-formed shape that collapses the inflatable balloon.

15. A method of claim 13, further comprising:
inflating an inflatable balloon of a balloon catheter through a flow path that traverses an elongated shaft of the balloon catheter, a central lumen of a central tube positioned within the inflatable balloon, an opening in the central tube and inflation ports of the central tube, and an interior of the inflatable balloon, the opening in the central tube being in fluidic communication with the central lumen, in fluidic communication with the elongated shaft, and positioned in a proximal direction from the inflation ports;
structurally supporting the inflatable balloon along a longitudinal axis of the balloon catheter with the central tube, the central tube being aligned with the longitudinal axis so that at least a portion of the central tube is positioned within the inflatable balloon; and
inhibiting inflation medium traversing the flow path from moving through the central lumen distal of the central tube.

16. The method of claim 15, further comprising:
extending the inflatable balloon in length in relation to the longitudinal axis by allowing an elastic element coupled to the central tube and shaft to self-elongate thereby sliding the central tube longitudinally in relation to the shaft; and
contracting the inflatable balloon in length in relation to the longitudinal axis by retracting a puller-wire connected to the central tube and extending through the shaft thereby compressing the elastic element along the longitudinal axis and sliding the central tube longitudinally in relation to the shaft.

17. The method of claim 15, further comprising:
sliding the central tube in relation to the elongated shaft to thereby extend and/or contract the inflatable balloon in length in relation to the longitudinal axis.

18. The method of claim 15, further comprising:
collapsing a set of splines made at least partially from a shape-memory material having a collapsed pre-formed shape that collapses the inflatable balloon.

* * * * *